(12) United States Patent
Barghouth et al.

(10) Patent No.: US 12,390,614 B2
(45) Date of Patent: *Aug. 19, 2025

(54) HUMIDIFICATION OF VENTILATOR GASES

(71) Applicants: Paul Barghouth, Santa Clara, CA (US); Michael Urner, Clovis, CA (US)

(72) Inventors: Paul Barghouth, Santa Clara, CA (US); Michael Urner, Clovis, CA (US)

(73) Assignee: SahaMed Technologies, LLC, Santa Clara, CA (US)

( * ) Notice: Subject to any disclaimer, the term of this patent is extended or adjusted under 35 U.S.C. 154(b) by 841 days.

This patent is subject to a terminal disclaimer.

(21) Appl. No.: 17/068,322

(22) Filed: Oct. 12, 2020

(65) Prior Publication Data
US 2021/0023327 A1    Jan. 28, 2021

Related U.S. Application Data

(63) Continuation-in-part of application No. 15/408,852, filed on Jan. 18, 2017, now Pat. No. 10,799,664, (Continued)

(51) Int. Cl.
*A61M 16/16*    (2006.01)
*A61M 16/08*    (2006.01)
(Continued)

(52) U.S. Cl.
CPC ...... *A61M 16/162* (2013.01); *A61M 16/0875* (2013.01); *A61M 16/109* (2014.02);
(Continued)

(58) Field of Classification Search
CPC .......... H05B 3/0071; H05B 3/28; H05B 3/80; H05B 2203/02; H05B 2203/021;
(Continued)

(56) References Cited

U.S. PATENT DOCUMENTS 2,070,728 A    2/1937  Hanft
2,782,290 A *  2/1957  Lannan ................... H01B 7/10
                                                        338/214
(Continued)

FOREIGN PATENT DOCUMENTS

CN    2168599 Y  *  6/1994
CN    207591073 U  *  7/2018
(Continued)

OTHER PUBLICATIONS

Hayes, et al. "Continuous nasal positive airway pressure with a mouth leak: effect on nasal mucosal blood flux and nasal geometry" Thorax, Nov. 1995; 50(11):1179-82).

*Primary Examiner* — Kathryn E Ditmer
(74) *Attorney, Agent, or Firm* — Edwin S. Flores; Daniel J. Chalker; Chalker Flores, LLP

(57) ABSTRACT

The present invention includes devices that relate to, for example, humidification systems for making humidified ventilator air that include a transparent or semi-transparent polymer-based heating element sleeve or sheet for the insulation of a tube delivering heated and humidified gas to a subject, comprising: a self-regulated heater and self-limiting heater, wherein the tubing is enveloped by the transparent heating sleeve, wherein the heating sleeve maintains at least one of: rates of relative humidity, absolute humidity and gas temperature, and wherein the heating sleeve envelops the tubing of inspiratory or expiratory limbs or ports connected to a mechanical ventilator providing gas to a subject.

10 Claims, 25 Drawing Sheets

Related U.S. Application Data which is a continuation of application No. 14/280,503, filed on May 16, 2014, now Pat. No. 9,561,341.

(60) Provisional application No. 61/824,815, filed on May 17, 2013.

(51) Int. Cl.
| | |
|---|---|
| *A61M 16/10* | (2006.01) |
| *F16L 53/38* | (2018.01) |
| *H05B 3/12* | (2006.01) |
| *H05B 3/18* | (2006.01) |
| *H05B 3/36* | (2006.01) |

(52) U.S. Cl.
CPC ........ *A61M 16/1095* (2014.02); *A61M 16/16* (2013.01); *A61M 16/161* (2014.02); *A61M 16/164* (2014.02); *F16L 53/38* (2018.01); *H05B 3/12* (2013.01); *H05B 3/18* (2013.01); *H05B 3/36* (2013.01); *A61M 2205/3368* (2013.01); *A61M 2205/3389* (2013.01)

(58) Field of Classification Search
CPC ... H05B 3/12; H05B 3/18; H05B 3/36; A61M 16/08; A61M 16/0875; A61M 16/1075; A61M 16/1085; A61M 16/16; F16L 53/38
See application file for complete search history.

(56) References Cited

U.S. PATENT DOCUMENTS

| | | | |
|---|---|---|---|
| 3,063,286 A | 11/1962 | Nerheim | |
| 3,962,381 A | 6/1976 | Farrish et al. | |
| 3,968,346 A | 7/1976 | Cooksley | |
| 4,110,419 A | 8/1978 | Miller | |
| 4,225,542 A * | 9/1980 | Wall | A61M 16/1075 261/DIG. 65 |
| 4,334,148 A * | 6/1982 | Kampe | H01C 1/02 264/105 |
| 4,441,027 A | 4/1984 | Richardson et al. | |
| 4,621,633 A * | 11/1986 | Bowles | A61M 16/1095 128/203.27 |
| 4,673,801 A * | 6/1987 | Leary | H05B 3/56 219/544 |
| 4,674,494 A | 6/1987 | Wiencek | |
| 4,700,054 A * | 10/1987 | Triplett | H05B 3/36 219/545 |
| 4,955,372 A | 9/1990 | Blackmer et al. | |
| 5,197,595 A * | 3/1993 | Coultas | H05B 3/36 219/535 |
| 5,309,900 A | 5/1994 | Knoch et al. | |
| 5,377,670 A * | 1/1995 | Smith | A62B 9/00 128/207.14 |
| 5,848,223 A * | 12/1998 | Carlson | F16L 11/24 219/535 |
| 5,933,574 A * | 8/1999 | Avansino | F16L 53/38 219/535 |
| 6,167,883 B1 | 1/2001 | Behran et al. | |
| 6,394,427 B1 | 5/2002 | Guetersloh et al. | |
| 8,206,337 B2 | 6/2012 | Blackhurst et al. | |
| 9,423,142 B2 | 8/2016 | Lee | |
| 9,561,341 B2 | 2/2017 | Visveshwara et al. | |
| 2006/0249212 A1 * | 11/2006 | Kressierer/Huber | A61M 16/0858 138/33 |
| 2008/0279540 A1 * | 11/2008 | Huang | A61M 16/1085 392/480 |
| 2009/0235440 A1 | 9/2009 | Udelhofen | |
| 2011/0259872 A1 * | 10/2011 | Wang | H05B 3/56 219/490 |
| 2012/0006209 A1 | 1/2012 | Mathey et al. | |
| 2013/0081626 A1 | 4/2013 | Pujol et al. | |
| 2014/0154134 A1 * | 6/2014 | Leyva | A61M 16/0816 128/203.29 |
| 2014/0338666 A1 * | 11/2014 | Visveshwara | A61M 16/16 128/203.26 |
| 2015/0020803 A1 * | 1/2015 | Dunlop | A61M 16/0875 128/203.14 |
| 2015/0366320 A1 * | 12/2015 | Bouix | H05B 3/34 219/385 |
| 2016/0015926 A1 | 1/2016 | Hermez et al. | |
| 2016/0354573 A1 * | 12/2016 | Buswell | A61M 16/1095 |
| 2017/0119992 A1 | 5/2017 | Visveshwara et al. | |
| 2020/0154526 A1 * | 5/2020 | Ester | H05K 3/4069 |

FOREIGN PATENT DOCUMENTS

| | | | |
|---|---|---|---|
| GB | 1461291 | 1/1977 | |
| JP | 2009197362 A | 9/2009 | |
| WO | WO-2010084183 A2 * | 7/2010 | ........ A61M 16/0875 |
| WO | WO-2020005151 A1 * | 1/2020 | ............ H05B 3/145 |

* cited by examiner

HUMIDIFICATION OF VENTILATOR GASES

CROSS REFERENCE TO RELATED APPLICATIONS

This patent application is a continuation-in-part of U.S. application Ser. No. 15/408,852, now U.S. Pat. No. 10,779,664, which is a continuation of U.S. application Ser. No. 14/280,503, filed May 16, 2014, now U.S. Pat. No. 9,561,341, which claims priority to U.S. Provisional Application No. 61/824,815, filed on May 17, 2013, which are herein incorporated by reference in their entirety.

STATEMENT OF FEDERALLY FUNDED RESEARCH

Not applicable.

FIELD OF THE INVENTION

The invention disclosed herein generally relates to improved humidification systems for producing humidified ventilator gases. The invention also relates to improved tubing designs that reduce condensation and loss of humidity of ventilator gases during delivery of the ventilator gases to an end user.

BACKGROUND OF THE INVENTION

The most common lung problem in a premature baby is respiratory distress syndrome (RDS), also known as hyaline membrane disease (HMD). A baby develops HMD when the lungs do not produce sufficient amounts of surfactant, a substance that keeps the tiny air sacs in the lung open. As a result, a premature baby often has difficulty expanding her lungs, taking in oxygen, and getting rid of carbon dioxide. HMD is common in premature babies because the lungs do not usually begin producing surfactant until about the $37^{th}$ week of pregnancy. Other factors that increase a baby's risk of developing HMD include Caucasian race, male sex, family history, and maternal diabetes. Fortunately, surfactant is now artificially produced and can be given to babies if doctors suspect they are not yet making surfactant on their own. Most of these babies also need extra oxygen and support from a ventilator, either through non-invasive continuous positive airway pressure (CPAP) or an invasive artificial airway, such as an endotracheal tube or tracheostomy tube. Non-invasive ventilation (NIV) is a mechanical ventilation modality that does not utilize an invasive artificial airway (endotracheal tube or tracheostomy tube).

During natural respiration, the air being inhaled is naturally humidified by the nasal cavity and epiglottis. However, when the native nasal passages are bypassed by invasive respiratory therapy, such as with the use of endotracheal tubes, the air must be artificially humidified. Inadequate airway humidification may have serious consequences or cause significant discomfort for patients. For example, one case study showed inspissated secretions, causing life-threatening airway obstruction in a patient using NIV for hypoxemic respiratory failure (Respir Care. 2000 May; 45(5):491-3).

The correct application of a humidification system may avoid the effects of ventilation-induced drying of the airway. Metaplastic changes and keratinization of the nasal epithelium and submucosa have been reported in patients on home NIV when the level of humidification was inadequate for long periods (Thorax. 1995 November; 50(11):1179-82.). These histopathological changes in the nasal mucosa occur relatively early after starting NIV in an acute setting and suggest that humidification should be considered even when only short-term use of NIV is expected.

Conventionally, humidification is done by a passover humidifier which is a system that passes air from the continuous positive air pressure (CPAP) over a room temperature body of water so as to pick up moisture. However, passover humidification only provides sub-optimal humidity.

After that, the humidified air then travels to the patient through tubes. However, when the moistened air cools down moving through the tubes, it condenses and holds less water (a problem known as 'rainout'). Hence, the conventional tubes in clinical use have a heating wire inside that runs along the length of the tube. Although this temperature control mechanism prevents some condensation, a water plug still forms in the line which interferes with the patient's respiratory therapy. Further, the use of a water reservoir in a passover humidification system raises health concerns, as the water reservoir tends to turn into a breeding ground for bacteria and must be replaced frequently.

Due to the above problems, the conventional respiratory therapy for the neonatal intensive care unit (ICU) exhibits subpar performance. The goal of this invention is to improve the humidity of the conventional passover humidification system, to eliminate condensation and rainout in the tubes and to decrease the amount of bacterial growth in the humidifier reservoir.

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

SUMMARY OF THE INVENTION

In one embodiment, the present invention includes a transparent or semi-transparent polymer-based heating element sleeve or sheet for the insulation of a tube delivering heated and humidified gas to a subject, comprising: a self-regulated heater and self-limiting heater, wherein the tubing is enveloped by the transparent heating sleeve, wherein the heating sleeve maintains at least one of: rates of relative humidity, absolute humidity and gas temperature, and wherein the heating sleeve envelops the tubing of inspiratory or expiratory limbs or ports connected to a mechanical ventilator providing gas to a subject. In one aspect, the heating sleeve or sheet further comprise a protective or connecting tube fitting over or enclosing the inspiratory or expiratory limbs or ports breathing tubes. In another aspect, the heating sleeve or sheet further comprises externally or internally insulating the tube which delivers heated and humidified gas to a subject. In another aspect, the heating sleeve or sheet is a transparent polymer-based heating element. In another aspect, the heating sleeve or sheet generates heat through a positive-temperature coefficient (PTC) heating element. In another aspect, a material within the heating sleeve or sheet consists of the PTC heating elements that are embedded in the transparent polymer. In another aspect, the heating sleeve or sheet is self-regulating, wherein each of one or more independent heating elements maintain a constant temperature without a need of electronic regulation. In another aspect, the heating sleeve or sheet is self-limiting, wherein the heating sleeve or sheet cannot exceed a certain temperature in any point, wherein the heating sleeve or sheet does not require overheating protection. In another aspect, the heating sleeve or sheet maintains a temperature between 20° C. to 60° C. in the tube. In another aspect, the heating sleeve or sheet maintains a temperature between 36° to 39° C. in the tube.

In another embodiment, the present invention includes a kit for retrofitting a tube for delivering heated and humidified gas to a subject, the kit comprising: a transparent polymer-based heating element sleeve or sheet for the insulation of a tube delivering heated and humidified gas to a subject, comprising: a self-regulated heater and self-limiting heater, wherein the tubing is enveloped by the transparent heating sleeve, wherein the heating sleeve maintains at least one of: rates of relative humidity, absolute humidity and gas temperature, and wherein the heating sleeve envelops the tubing of inspiratory or expiratory limbs or ports connected to a mechanical ventilator providing gas to a subject. In one aspect, the kit further comprises a protective or connecting tube fitting over or enclosing the inspiratory or expiratory limbs or ports breathing tubes. In one aspect, the kit further comprises externally or internally insulating the tube which delivers heated and humidified gas to a subject. In one aspect, the heating sleeve or sheet generates heat through a positive-temperature coefficient (PTC) heating element. In one aspect, a material within the heating sleeve or sheet consists of the PTC heating elements that are embedded in the transparent polymer. In one aspect, the heating sleeve or sheet is self-regulating, wherein each of one or more independent heating elements maintain a constant temperature without a need of electronic regulation. In one aspect, the heating sleeve or sheet is self-limiting, wherein the heating sleeve or sheet cannot exceed a certain temperature in any point, wherein the heating sleeve or sheet does not require overheating protection. In one aspect, the heating sleeve or sheet maintains a temperature between 20° C. to 60° C. in the tube. In one aspect, the heating sleeve or sheet maintains a temperature between 36° to 39° C. in the tube.

In another embodiment, the present invention includes a system for humidifying ventilator air, comprising a chamber, a base, a central cylinder and a helical inclining plane, wherein the chamber comprises an air inlet for receiving air from an air source, an air outlet for releasing humidified air, and an inner wall; wherein the base comprises an inner surface, the inner surface and the inner wall forming a sealed space capable of holding water and air; wherein the central cylinder comprises a bottom and a side, the bottom attaching to the inner surface of the base; wherein the helical inclining plane comprises a helical center, an inner edge and an outer edge, the central cylinder passing through the helical inclining plane at the helical center; the inner edge attaching to the side of the central cylinder; wherein the outer edge of the helical inclining plane engages with the inner wall of the chamber to form a helical inclining tunnel, a lower end of the tunnel opening towards the air inlet and a upper end of the tunnel opening towards the air outlet; and transparent or semi-transparent polymer-based heating element sleeve or sheet for the insulation of a tube delivering heated and humidified gas to a subject, comprising: a self-regulated heater and self-limiting heater, wherein the tubing is enveloped by the transparent heating sleeve, wherein the heating sleeve maintains at least one of: rates of relative humidity, absolute humidity and gas temperature, and wherein the heating sleeve envelops the tubing of inspiratory or expiratory limbs or ports connected to a mechanical ventilator providing gas to a subject.

In another embodiment, the present invention includes a method for heating and humidifying ventilator air, comprising a chamber, a base, a central cylinder, a helical inclining plane, and a tube comprising: providing the chamber comprises an air inlet for receiving air from an air source, an air outlet for releasing humidified air, and an inner wall; wherein the base comprises an inner surface, the inner surface and the inner wall forming a sealed space capable of holding water and air; wherein the central cylinder comprises a bottom and a side, the bottom attaching to the inner surface of the base; wherein the helical inclining plane comprises a helical center, an inner edge and an outer edge, the central cylinder passing through the helical inclining plane at the helical center; the inner edge attaching to the side of the central cylinder; wherein the outer edge of the helical inclining plane engages with the inner wall of the chamber to form a helical inclining tunnel, a lower end of the tunnel opening towards the air inlet and a upper end of the tunnel opening towards the air outlet; and surrounding at least partially the tube with a transparent or semi-transparent polymer-based heating element sleeve or sheet for the insulation of a tube delivering heated and humidified gas to a subject, comprising: a self-regulated heater and self-limiting heater; wherein the tubing is enveloped by the transparent heating sleeve; wherein the heating sleeve maintains at least one of: rates of relative humidity, absolute humidity and gas temperature; and wherein the heating sleeve envelops the tubing of inspiratory or expiratory limbs or ports connected to a mechanical ventilator providing gas to a subject.

Systems described herein are provided by way of example and should not in any way limit the scope of the invention.

In one aspect, a system for humidifying ventilator air is described. The system comprises a chamber, a base, a central cylinder and a helical inclining plane. The chamber comprises an air inlet for receiving air from an air source, an air outlet for releasing humidified air, and an inner wall. The base comprises an inner surface, the inner surface and the inner wall forming a sealed space capable of holding water and air. The central cylinder comprises a bottom and a side, the bottom attaching to the inner surface of the base. The helical inclining plane comprises a helical center, an inner edge and an outer edge, the central cylinder passing through the helical inclining plane at the helical center; the inner edge attaching to the side of the central cylinder. The outer edge of the helical inclining plane engages with the inner wall of the chamber to form a helical inclining tunnel, a lower end of the tunnel opening towards the air inlet and an upper end of the tunnel opening towards the air outlet.

In another aspect, a tube for delivering humidified air is described. The tube comprises an air tube and a heat blanket. The air tube is enveloped by the heat blanket; and the heat blanket is configured to warm up the air tube to a certain temperature.

The details of one or more embodiments of the disclosure are set forth in the accompanying drawings and the description below. Other features, objects, and advantages will be apparent from the description and drawings, and from the claims.

BRIEF DESCRIPTION OF THE SEVERAL VIEWS OF THE DRAWINGS

Those of skill in the art will understand that the drawings, described below, are for illustrative purposes only. The drawings are not intended to limit the scope of the present teachings in any way.

FIG. 10A shows first a positive-temperature coefficient (PTC) heating element of the present invention, and FIG. 10B shows a second a PTC heating element of the present invention.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described.

Provided herein are humidification systems and air delivery tubing for ventilator air. According to a first aspect of the present invention, a humidification system is described.

FIGS. 4A through 4D illustrate the humidification system according to one embodiment of the invention. As shown in the figures, the humidification system comprises at least a top portion (401) and a bottom portion (402). The top and bottom portions can be assembled into a sealed unit for air-water interaction and humidification.

Figure 3A:
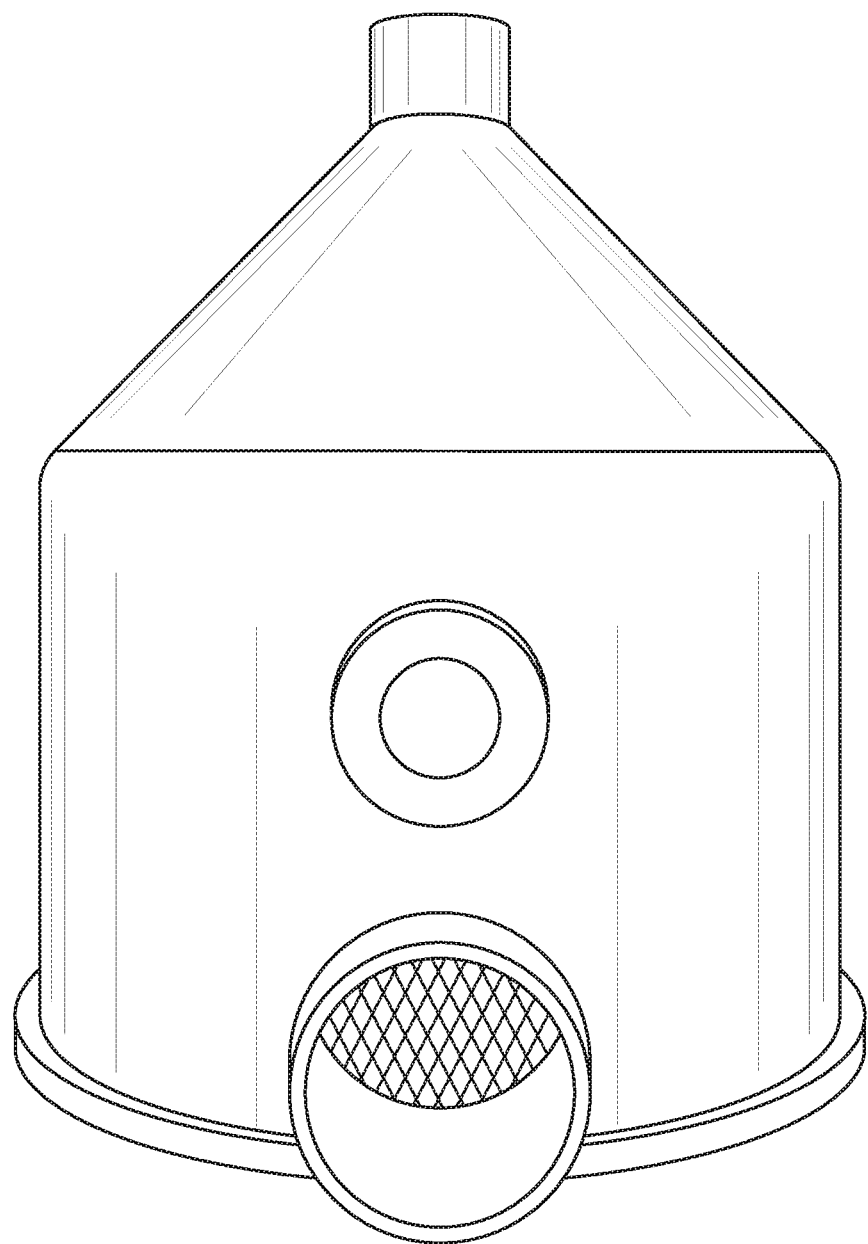
FIG. 3A is a photo of an assembled prototype of the humidification system according to one embodiment of the present invention. This photo shows the air inlet, the air outlet, and the water level sensor port, all of which are attached to the air-water interaction unit of the system.
Figure 3B:
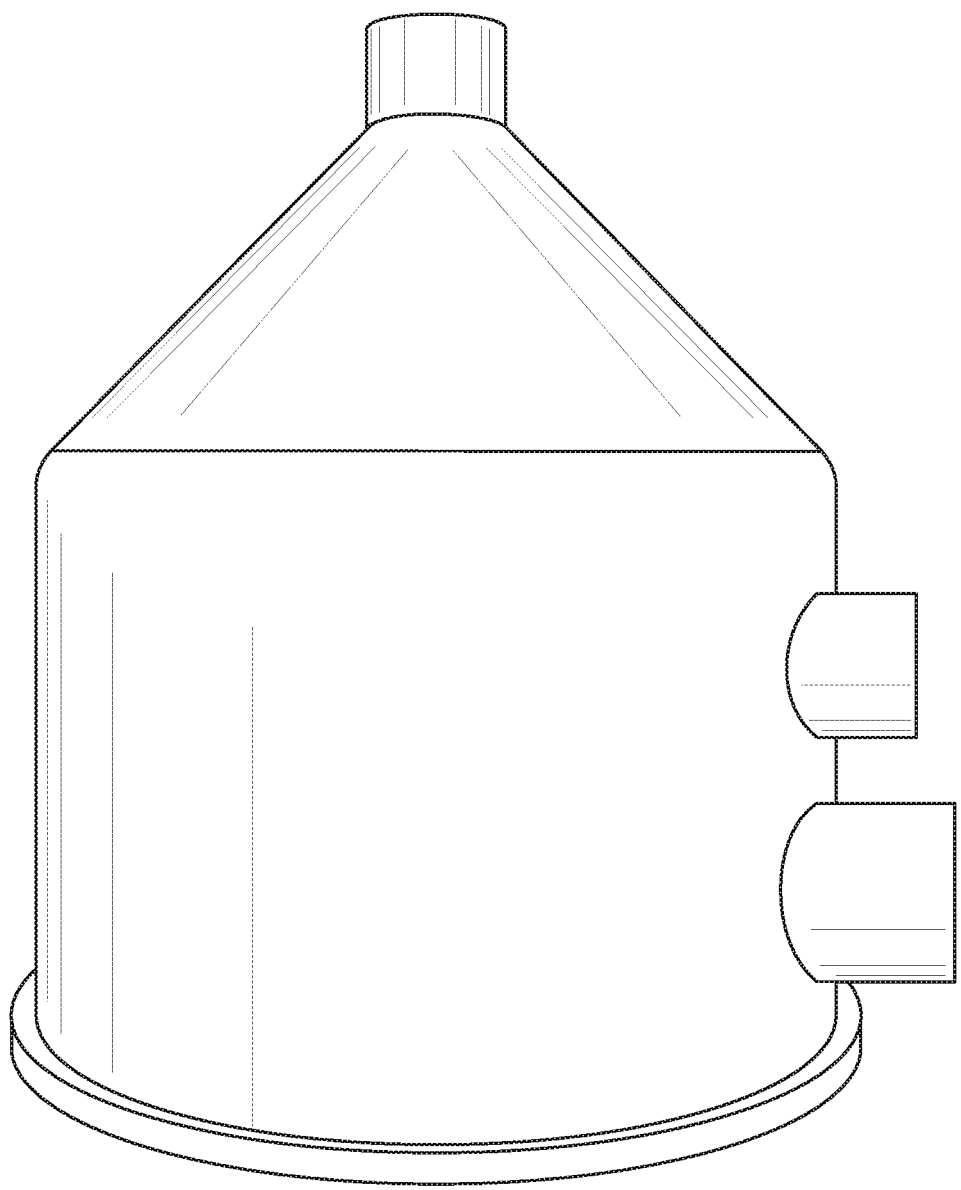
FIG. 3B is a photo of an assembled prototype of the humidification system according to one embodiment of the present invention. This photo shows the air inlet, the air outlet, the water level sensor port, and the water inlet, all of which are attached to the air-water interaction unit of the system.
Figure 3C:
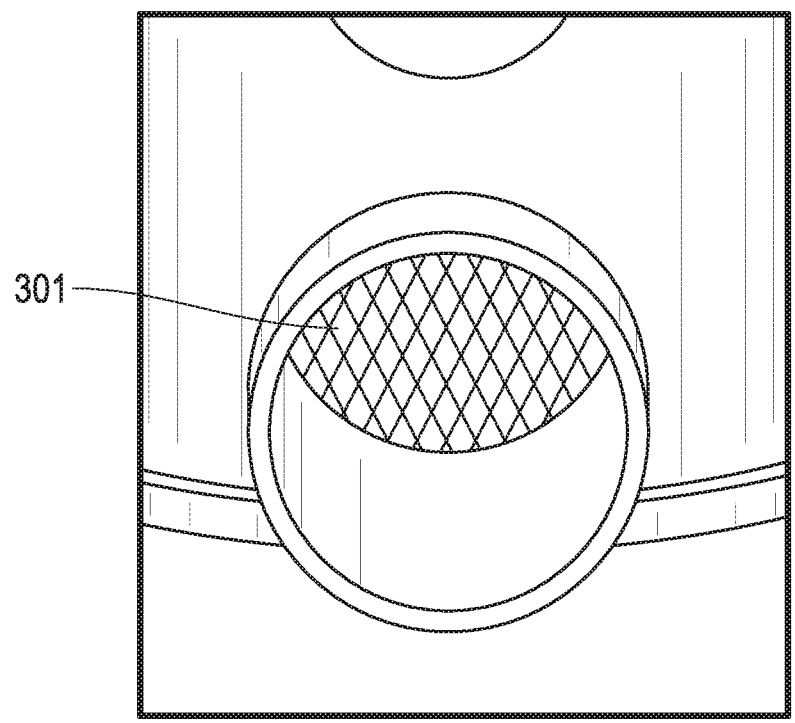
FIG. 3C is a photo of the air inlet of the humidification system according to one embodiment of the present invention. The inlet has an air mesh positioned across a transverse section of inlet channel next to the air-water interaction unit of the system.
Figure 4A:
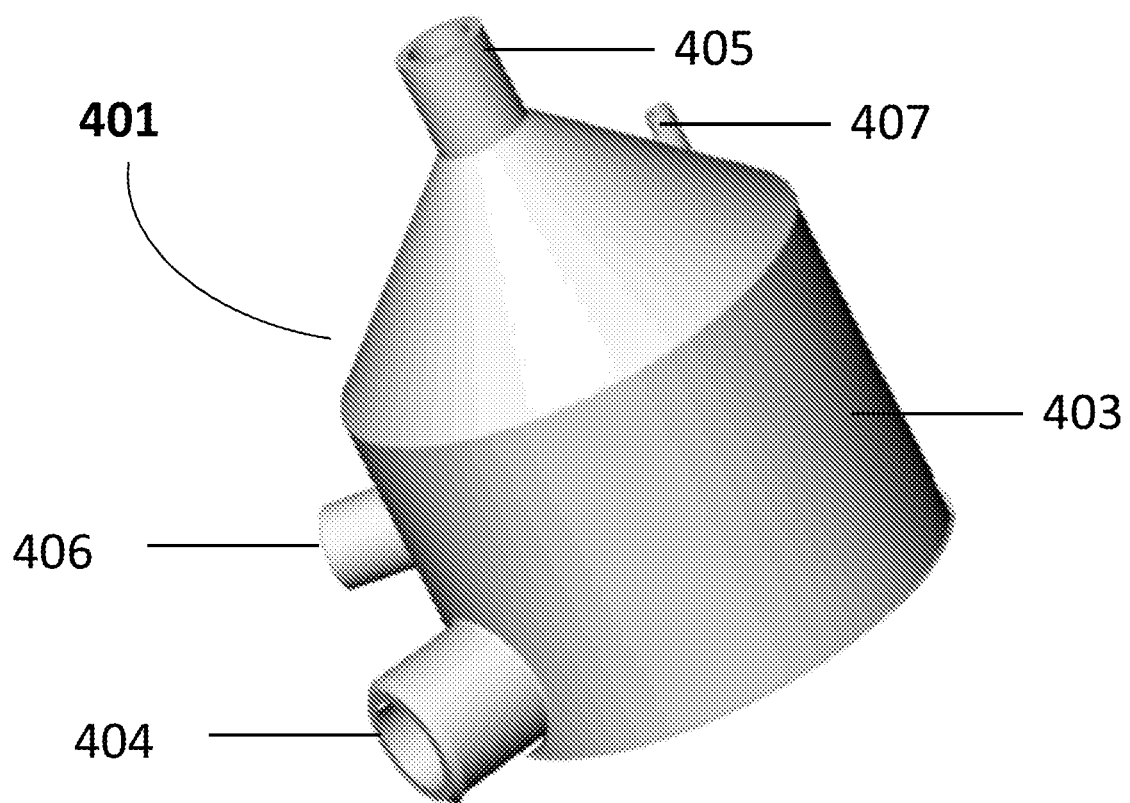
FIG. 4A is a perspective drawing of a top portion of the humidification system according to one embodiment of the present invention. This portion includes an outer wall of the air-water interaction unit, an air inlet, an air outlet, a water level sensor connector and a water inlet.

As shown in FIG. 4A, the top portion (401) comprises a hollow chamber (403); an air inlet (404) and an air outlet (405). The chamber (403) has a cone-shaped top and a cylinder-shaped bottom. The air inlet (404) is attached to the bottom of the cylindrical part of the chamber (403). As shown in FIG. 3C, the air inlet (404) is connected to the chamber (403) through an air mesh (301) positioned at a transverse section of the inlet channel. The air outlet (405) is attached at the tip of the conical part of the chamber (403).

In some embodiments, the top portion (401) of the humidification system further comprises a port (406) for connecting a water level sensor, and a water inlet (407). The water level sensor port (406) is attached to the middle of the cylindrical part of the chamber (403), and the water inlet (407) is attached to the side of the conical part of the chamber (403).

Figure 4B:
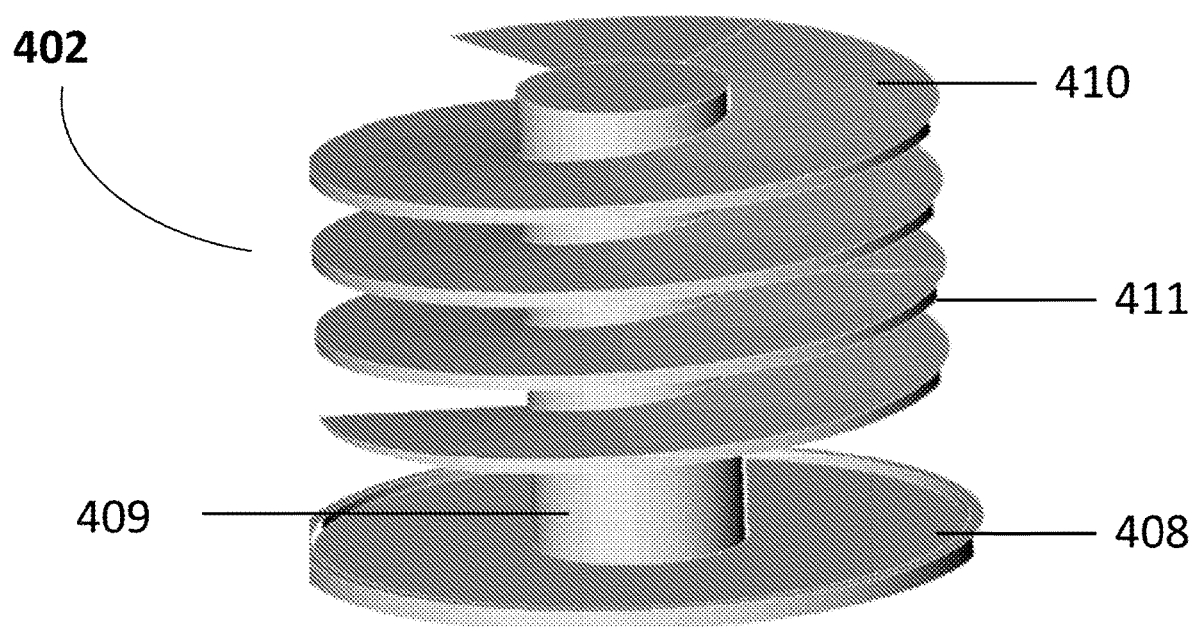
FIG. 4B is a perspective drawing of a bottom portion of the humidification system according to one embodiment of the present invention. This portion includes a base, a central cylinder and a helical stair plane.

As shown in FIG. 4B, the bottom portion (402) of the humidification system comprises a base (408); a central cylinder (409); and a helical inclining plane (410) with multiple layers. The base (408) assumes a round shape, and is capable of engaging with cylindrical part of the top portion (401) to form a sealed unit for air-water interaction. The central cylinder (409) is attached at the center of the base (408). The height of the central cylinder (409) is the same as the height of the cylindrical part of the top portion (401). The diameter of the central cylinder (409) is smaller than the diameter of the cylindrical part of the top portion (401). The helical inclining plane (410) is attached to the central cylinder (409) with the central cylinder (409) passing through the helical center of the helical inclining plane (410).

Figure 4C:
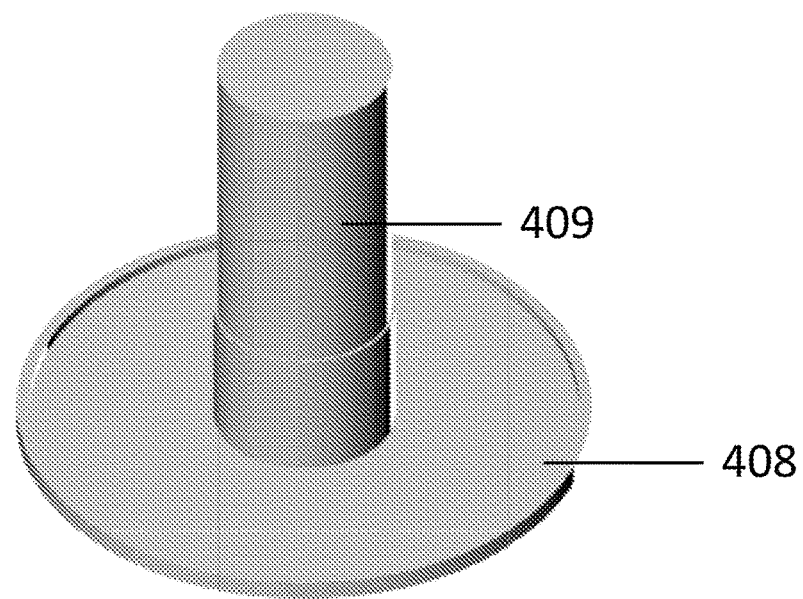
FIG. 4C is a perspective drawing of a base and a central cylinder of the humidification system according to one embodiment of the present invention.
Figure 4D:
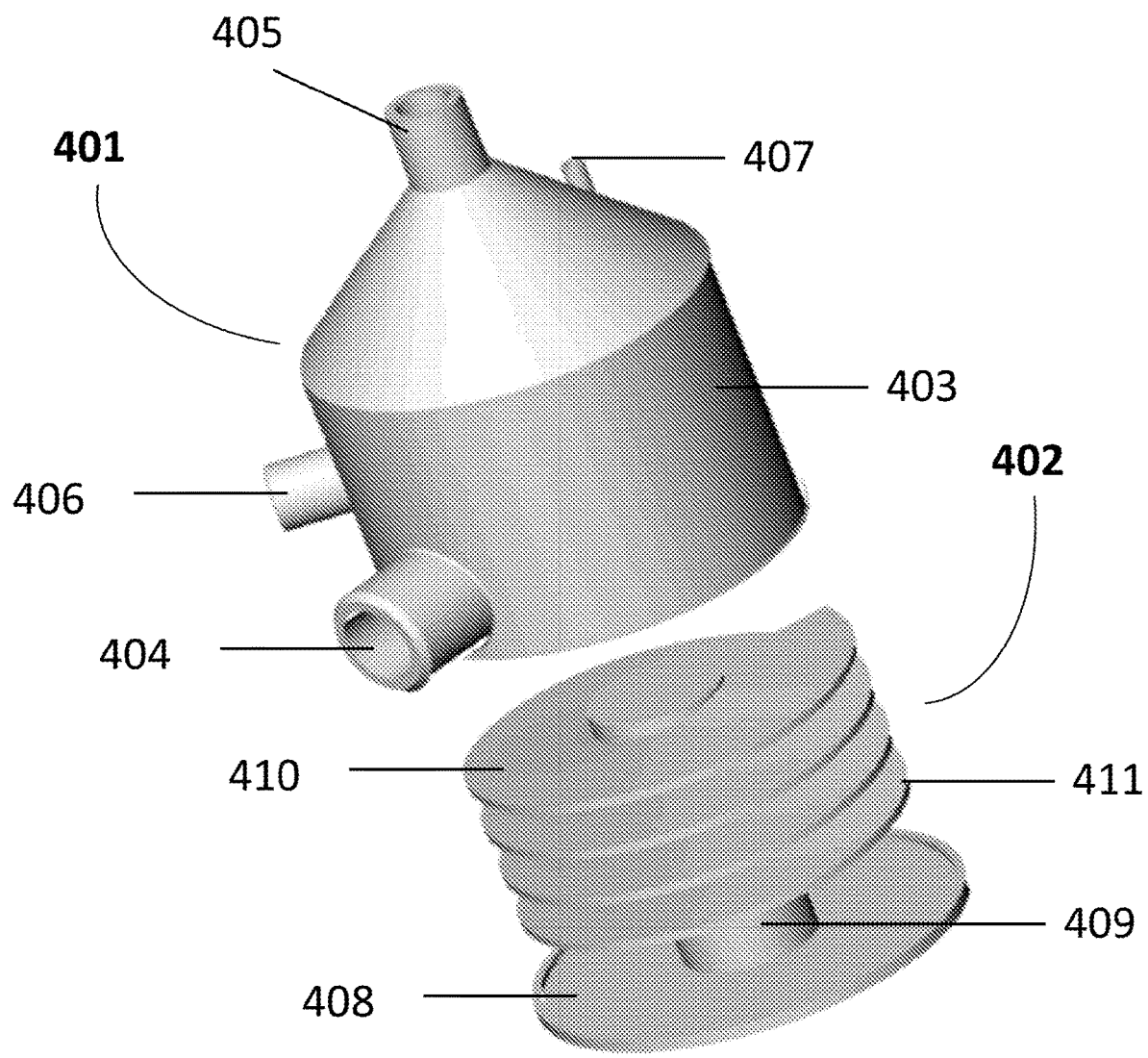
FIG. 4D is a perspective drawing of the humidification system according to one embodiment of the present invention, showing both the top and bottom portions of the system.

As shown in FIG. 4D, when the top portion (401) and bottom portion (402) are assembled together, the central cylinder (409) and the helical inclining plane (410) fit into the chamber (403), and the base (408) seals the chamber (403) at the bottom of its cylindrical part. The edge (411) of the helical inclining plane (410) presses tightly against the inner surface of the cylindrical part of the chamber (403).

Thus, when assembled together, the inner wall of the chamber (403), the helical inclining plane (410) and the central cylinder (409) form a helical inclining tunnel. The lower end of the tunnel opens towards the air inlet (404), and the upper end of the tunnel opens towards the air outlet (405) of the system.

According to some embodiments of the present invention, when in use, the chamber (403) of the humidification system is filled with water. The water level is kept below the conical part of the chamber (403), so that the chamber (403) contains a body of air next to the air outlet (405).

An air supply delivers ventilator gases to the system through the air inlet (404). When air passes through the air mesh (301) into the chamber (403) and contacts with water, the airstream breaks into tiny air bubbles. Then the bubbles enter the lower end of the helical inclining tunnel and move along tunnel to reach the water surface at the upper end of the tunnel and burst into the body of air at the conical part of the chamber (403). During this process, the air picks up moisture and gets humidified. The cone-shaped top of the chamber (403) allows more laminar flow of humidified air, as well as prevents condensation from forming on the angled surface of the chamber (403). The humidified air then exits the humidification system through the air outlet (405) and is delivered through an inspiratory line to a patient in need.

In some embodiments, the humidification system is equipped with a water level sensor for detecting and adjusting decrease in the water level, such as due to evaporation. In some embodiments, the water level sensor is pre-set with threshold values. When the water level decreases below the threshold, the water level sensor sends a warning signal. For example, in some embodiments, the water level sensor is attached to the chamber (403) via the port (406). As shown in FIG. 4A, in some embodiments, the port (406) is positioned at the middle height of the cylindrical part of the chamber (403). When water level decreases to below the middle height of the cylindrical part of the chamber (403), the water level sensor sends a warning signal.

In some embodiments, the water level sensor further activates a mechanism that refills water into the chamber (403) through the water inlet (407) attached to the conical part of the chamber (403). When the water level is adjusted, the sensor deactivates the refill mechanism until the water level decreases to the threshold again.

In some embodiments, the water in the humidification system is heated. As shown in FIG. 4C, in some embodiments, the base (408) of the system can be a metal heat plate, which increases the temperate of the water in the system. In some embodiments, the central cylinder (409) can be made of a thermal conductive metal, which helps to establish a more even heat distribution in the longitudinal direction in the chamber. In these embodiments, the ventilator gases, when passing through the heated water body as small bubbles, get both humidified and warmed up to a certain temperature, such as the physiological temperature suitable for a respiratory therapy.

In some embodiments, the surface of the water-air interaction unit is coated with antimicrobial metals, such as copper and silver. In some embodiments, the surface of the base (408) is coated with an antimicrobial metal. In other embodiments, the surface of the central cylinder (409) is coated with an antimicrobial metal. In other embodiments, the surface of the helical inclining plane (410) is coated with an antimicrobial metal. In other embodiments, the inner surface of the chamber (403) is coated with an antimicrobial metal. In yet other embodiments, two or more of the above mentioned surfaces are coated with an antimicrobial metal.

According to some embodiments of the present invention, the thickness of the antimicrobial coating is carefully examined and controlled. A metal coating that is too thin cannot produce sufficient ionic cloud to control bacterial growth in water, whereas a metal coating that is too thick risks the possibility of being peeled off and inhaled by a patient.

Accordingly, in some embodiments, the antimicrobial metal is silver. In some embodiments, the silver coating has a thickness of less than 3 mm. In other embodiments, the thickness of the silver coating is less than 1 mm. In yet other embodiments, the thickness of the silver coating is less than 0.5 mm. In some embodiments, the thickness of the silver coating ranges from about 0.5 mm to about 1 mm. In other embodiments, the silver coating has a thickness of about 0.5 mm. In other embodiments, the silver coating has a thickness of about 1 mm.

In some embodiments, one or more components of the humidification system, including the chamber (403), base (408), central cylinder (409), and helical inclining plane (410), are made of a metal material, such as aluminum. In other embodiments, the chamber (403) is made of a plastic material, such as DL-polylactide with 50:50 ratio of D-PLA and L-PLA. In other embodiments, the helical inclining plane (410) is made of a plastic material.

Figure 1:
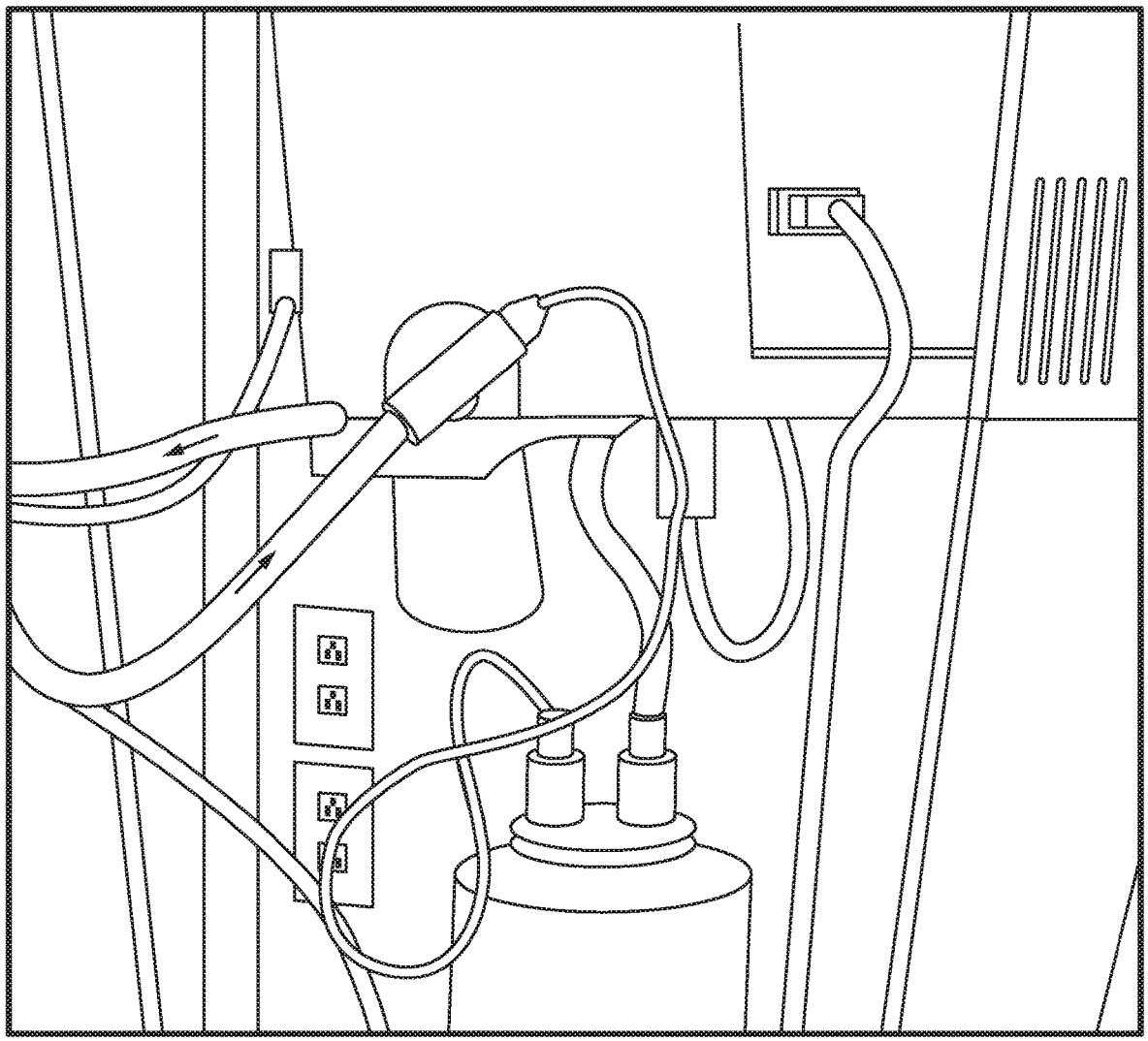
FIG. 1 depicts an exemplary setup of a ventilation system equipped with a conventional passover humidifier.

As apparent from above, the humidification system according to the present invention gas many advantages as compared to the conventional system. FIG. 1 shows a clinical ventilator equipped with a conventional passover humidifier and conventional heat-wire tubes. As shown in the figure, the humidifier has a plastic water chamber and an aluminum heat plate positioned at the bottom of the chamber. Both the air inlet and air outlet connect to the top of the chamber. When in use, the chamber is filled with a body of water. The heat plate is set to heat up the water to a certain temperature. A ventilator passes air through the humidifier via continuous positive air pressure. Particularly, ventilator air flows into the humidifier through the air inlet, picks up moisture and heat when bubbling up in the water or passing across the water surface, and flows into the inspiratory line of the ventilator through the air outlet. As shown in the figure, massive condensation builds up along the inspiratory line which delivers the warm humidified air to a patient.

Figure 2:
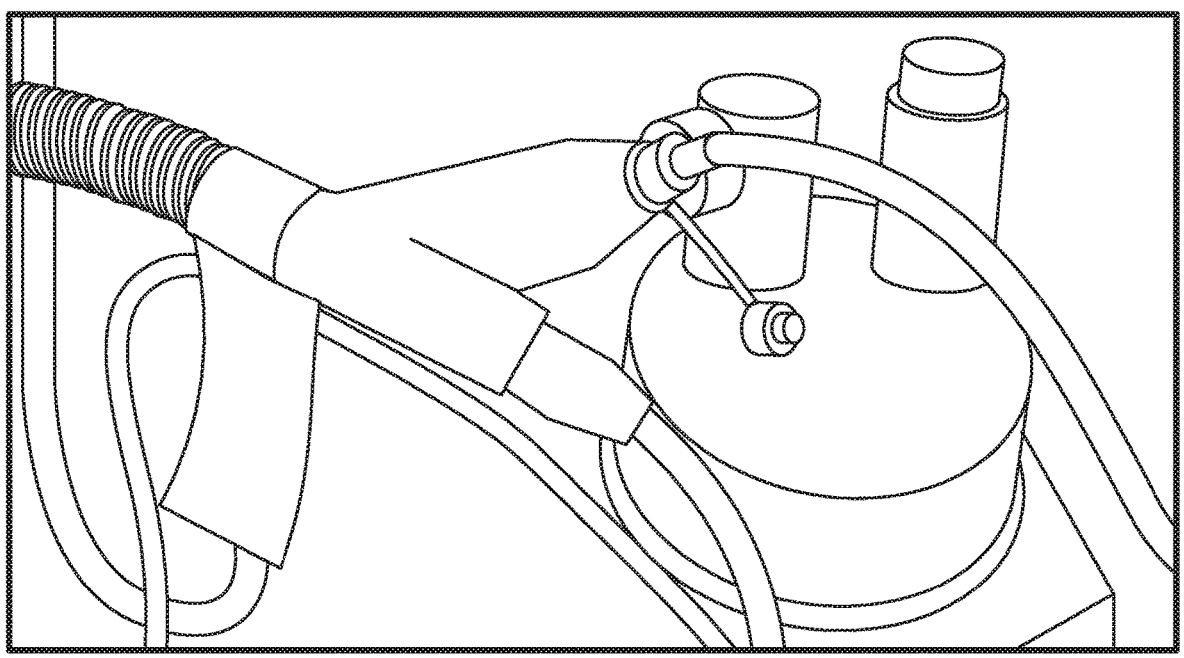
FIG. 2 depicts massive condensation on the tubing and water chamber of the ventilation system of FIG. 1 due to heat loss in the humidified air.

FIG. 2 is a close-up photo of the conventional passover humidifier, showing the water chamber, heat plate, air inlet, air outlet, and a short piece of inspiratory tube connected to the outlet. As can be seen from the figure, massive condensation and water rain-out accumulate within the water chamber, air outlet and inspiratory tube.

Therefore, in the conventional system, inlet airstream passes through the body of water in the chamber as large singular bubbles, or simply passes above the water surface. In contrast, the design of the present invention positions an air mesh (301) across the air inlet (404), which breaks the inlet airstream into large numbers of tiny air bubbles, dramatically increasing the surface area of air-water interaction. Further, the conventional humidifier does not define the pathway through which the inlet air travels in the body of water. Hence, once the inlet air contacts with water, it bubbles up directly towards the water surface. In contrast, the design of the present invention defines a helical inclining tunnel within the chamber (403), through which the tiny air bubbles must travel to reach the water surface. This significantly increases the time for air-water interaction. These designs of the present invention significantly improve the efficiency of humidification as compared to a conventional passover humidifier.

Additionally, the conventional system only heats up the water from the bottom of the chamber. Hence, air temperature above the water surface in the chamber is much lower than the heating temperature or water temperature at the bottom of the chamber. Using the conventional humidifier shown in FIGS. 1 and 2 as an example, when the heat plate is set to the physiological temperature of 37° C., the air temperature measured at the air outlet of the chamber can be as low as 25° C. Heat loss in the humidified air is a major cause of condensation. Hence, the design of the present invention improves this problem by including the central column (409), which heats up with the base (408) and thus helps to establish a more even distribution of heat in the longitudinal direction within the chamber (403). Further, the cone-shaped top of the chamber (403) helps rainout water, if any, to run back into the body of water in the chamber (403) more quickly. These designs result in a more precisely controlled temperature of ventilator air that an end user receives and less condensation buildup within the humidification system and inspiratory tubing of the present invention.

Finally, the conventional humidifier lacks a mechanism that inhibits bacterial growth within the warm and wet environment of the water chamber. In contrast, the humidification system according to the present invention has an antimicrobial material applied to the inner surface of the water chamber (403), which decreased the risk of causing additional health problems for a patient receiving inspiratory therapy.

According to a second aspect of the present invention, a tubing design for delivering humidified gases is described. The tubing can reduce or eliminate condensation and water rain-out in the respiratory line of the ventilator system.

Condensation forms when there is a difference in temperature between two media, where the warmer media contains a degree of moisture. This moisture typically consists of water droplets which contain a large amount of energy, such that they remain in the gas phase. When the temperature drops, the moisture condenses by having this energy absorbed by the cooler media and becomes water. In a ventilator system, condensation occurs at the walls of the tube, since the warm media (warmed humidified air) flows within the tube, and the cooler media is located in the environment outside the tube. Overtime, condensation builds up within the tubing system, and creates water pockets or plugs at lower points of the tube, which decreases the functionality of the ventilator system and reduces humidity of air that enters into a patient's respiratory system.

Figure 7A:
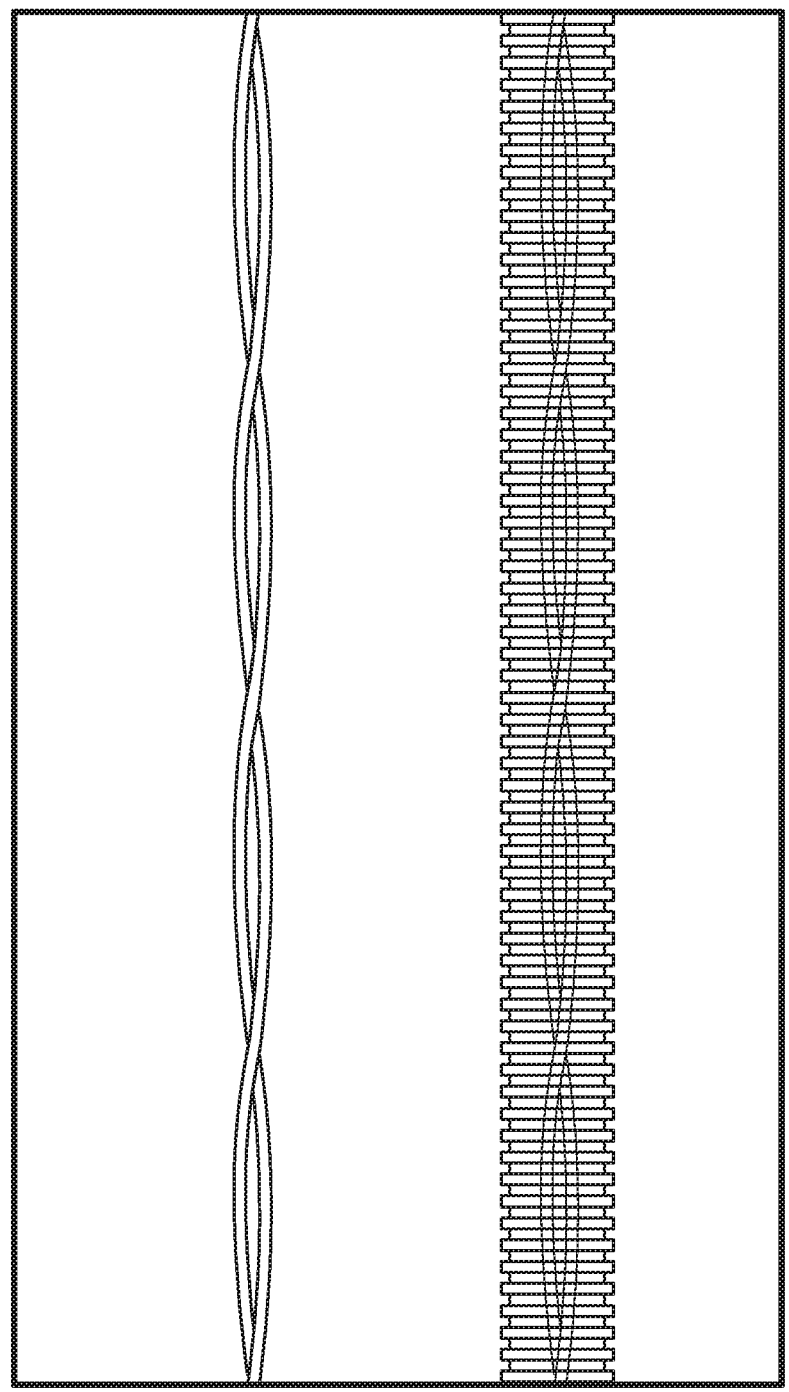
FIG. 7A is a photo of a conventional air tube used for delivering humidified air. The air tube contains an insulated heating wire inside that runs along the length of the tube.

To circumvent the condensation problem, a conventional ventilator system uses a hot wire tube to deliver humidified air. The heat-wire tube contains a heating wire that runs along the length of the tube and heats up the air from inside the tube. FIG. 7A shows a heating wire and a tube containing the heating wire inside.

Figure 7B:
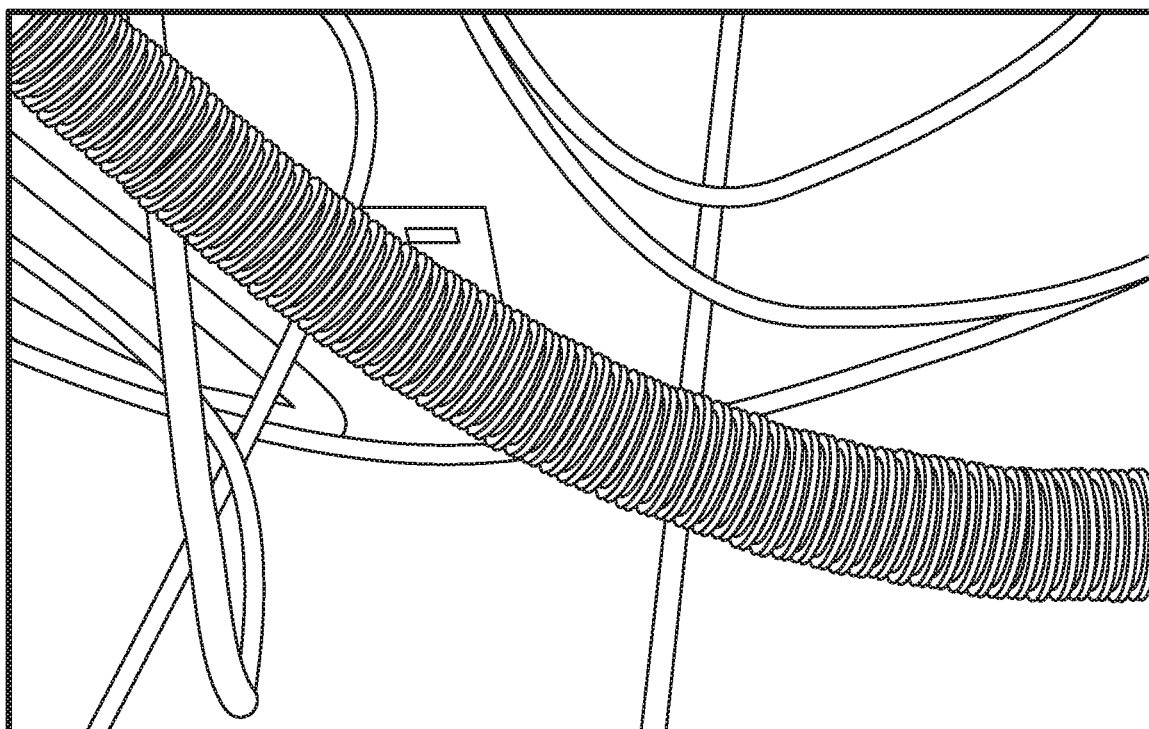
FIG. 7B is a photo showing condensation buildup within the conventional air tube.

This temperature control mechanism reduces the amount of condensation to some extent by heating the humidified air to a level which helps the water maintains its energy and remains as steam throughout the tube. However, this mechanism does not address the fundamental issue that causes condensation. The cooler temperature from the exterior of the tube still cools the inner lining of the tube, therefore causing a heat flux which leads to the drop in temperature and condensation. FIG. 7B shows a conventional heat-wire tube with condensed water accumulating at a lower point.

Figure 7C:
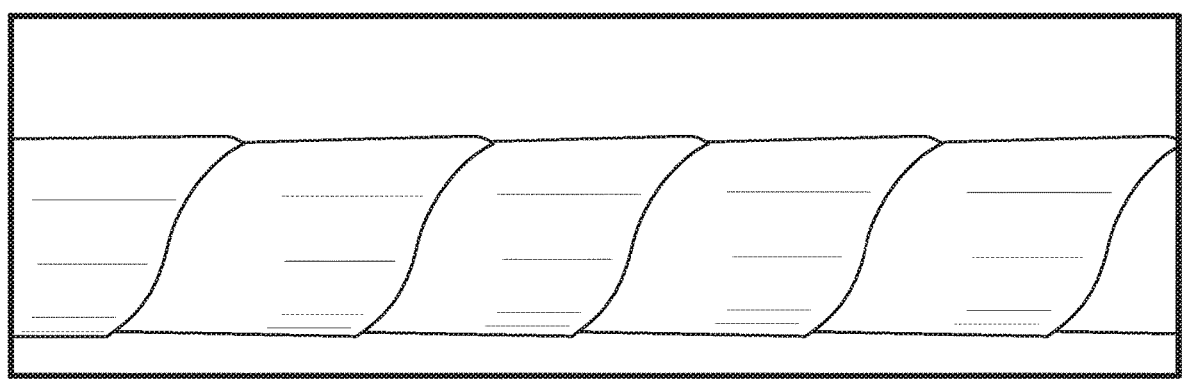
FIG. 7C is a photo of an air tube used for connecting the humidification and ventilation system according to one embodiment of the present invention. A heat blanket twines around and wraps the air tube.
Figure 8A:
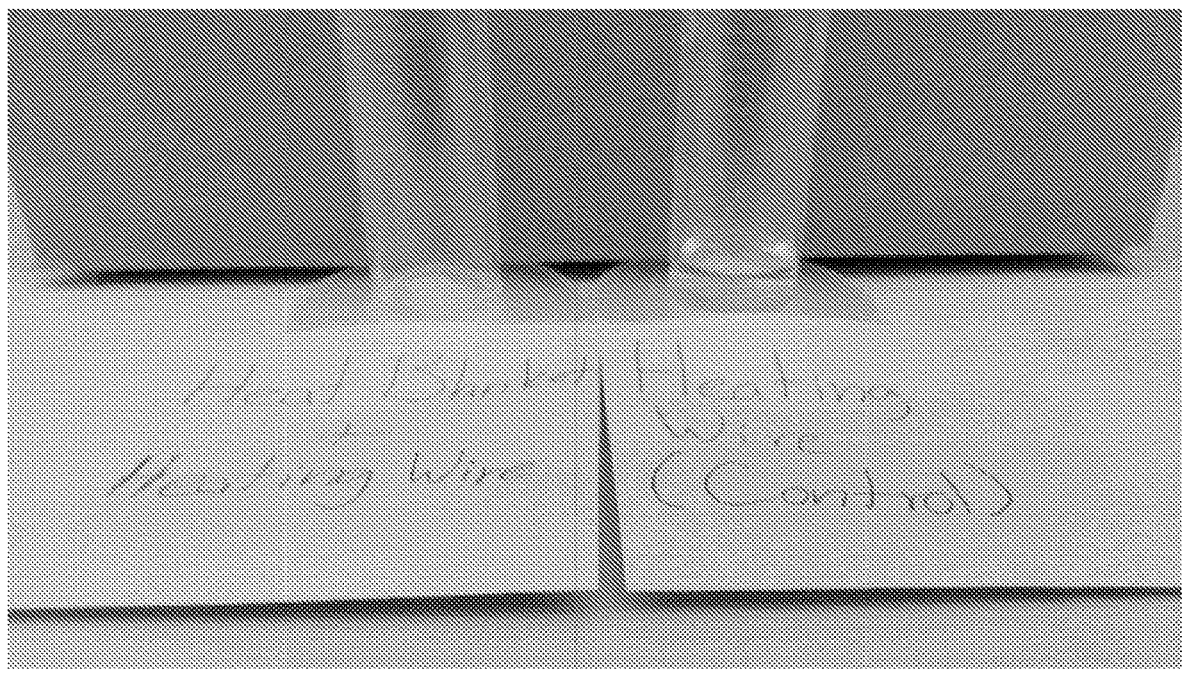
FIG. 8A shows the volumes of condensed water collected from the conventional heat wire tube and a tube equipped with both a heat wire and a heat blanket.
Figure 8B:
FIG. 8B shows the volumes of condensed water collected from a bare tube and a tube equipped with a heat blanket.

The tubing design of the present invention uses an external heat source to maintain the temperature within the walls of the tube. Particularly, as shown in FIG. 7C, the current design implements a heat blanket that surrounds and envelops the entire exterior of the tube. Instead of the heat coming from the inside of the tubes, which leaves the exterior exposed to heat loss to the outside environment, the heat blanket provides heat externally and warms the walls of the tubing. Thus, the heat blanket essentially maintains a constant temperature along the exterior of the tube, such that there is little to no temperature difference between the exterior and interior of the tube, thereby significantly reducing the amount of condensation within the system. In some embodiments, the heat blanket tubing of the present invention also contains a heat wire running within the tube.

In some embodiments, the heat blanket is made of silicon, with heating elements, such as heating wires, embedded within. In some embodiments, the heating blanket further comprises a heat insulating layer that covers the exterior of the blanket to prevent scald of a user. In some embodiments, the insulating layer can be made of bamboo. In some embodiments, the tubing is made of a plastic material, such as polyhydroxyalkanoate. In other embodiments, the tubing is made of a polymer material, such as silver polymer.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Humidification Tests

The humidification system of the present invention (referred to as the "new humidifier" in the examples) was tested for efficiency of humidification and temperature maintenance. The new humidifier was connected to a ventilator air source, and tested at three different (high, medium and low) air flow velocities. The medium air flow was about the same speed as normal human breath. The high air flow was twice as fast as the medium flow rate, and the low air flow was half of the medium flow rate. At each flow rate, the heating plate of the humidifier was set to 45° C., and the system was let run for 1 hour. Absolute humidity and temperature at the air outlet of the humidifier were measured every 10 minutes during the hour. The same experimental setting and protocol were applied to collect data from a conventional passover humidifier (referred to as the "old humidifier" in the examples).

Figure 5A:
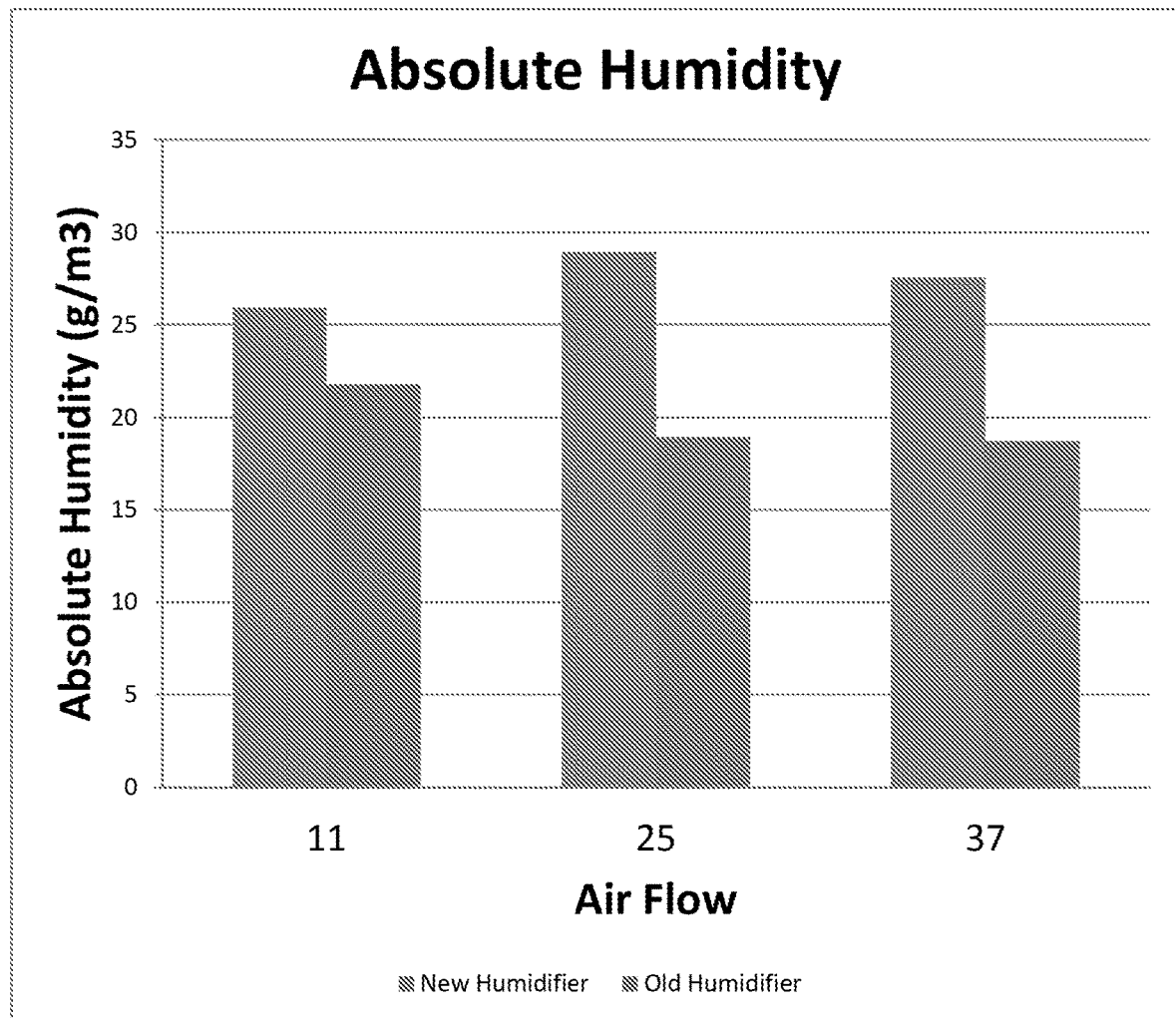
FIG. 5A illustrates improved absolute humidity of humidified air produced by the humidification system according to one embodiment of the invention as compared to a conventional passover humidifier.
Figure 5B:
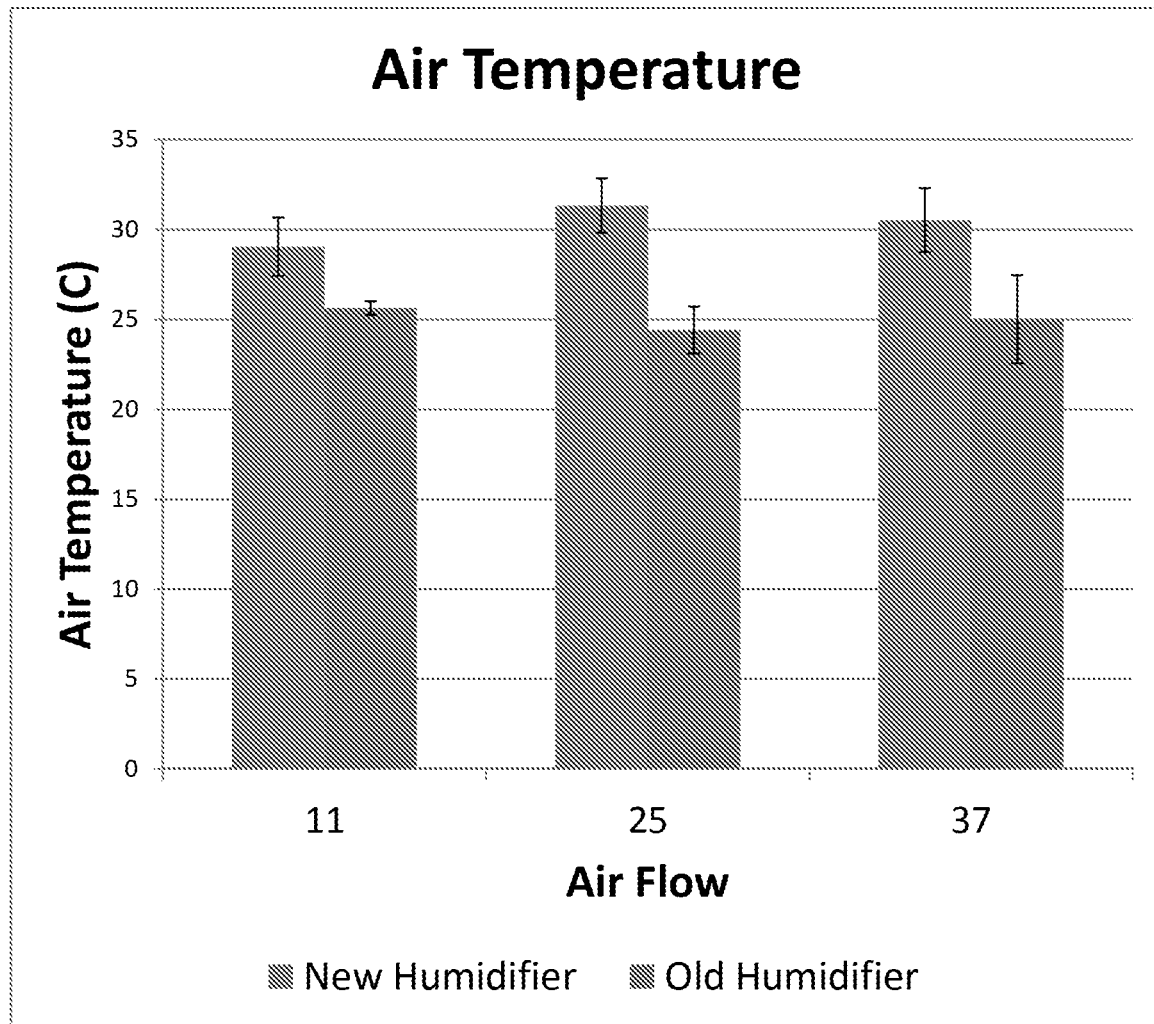
FIG. 5B illustrates improved maintenance of temperature of humidified air produced by the humidification system according to one embodiment of the invention as compared to a conventional passover humidifier.
Figure 5C:
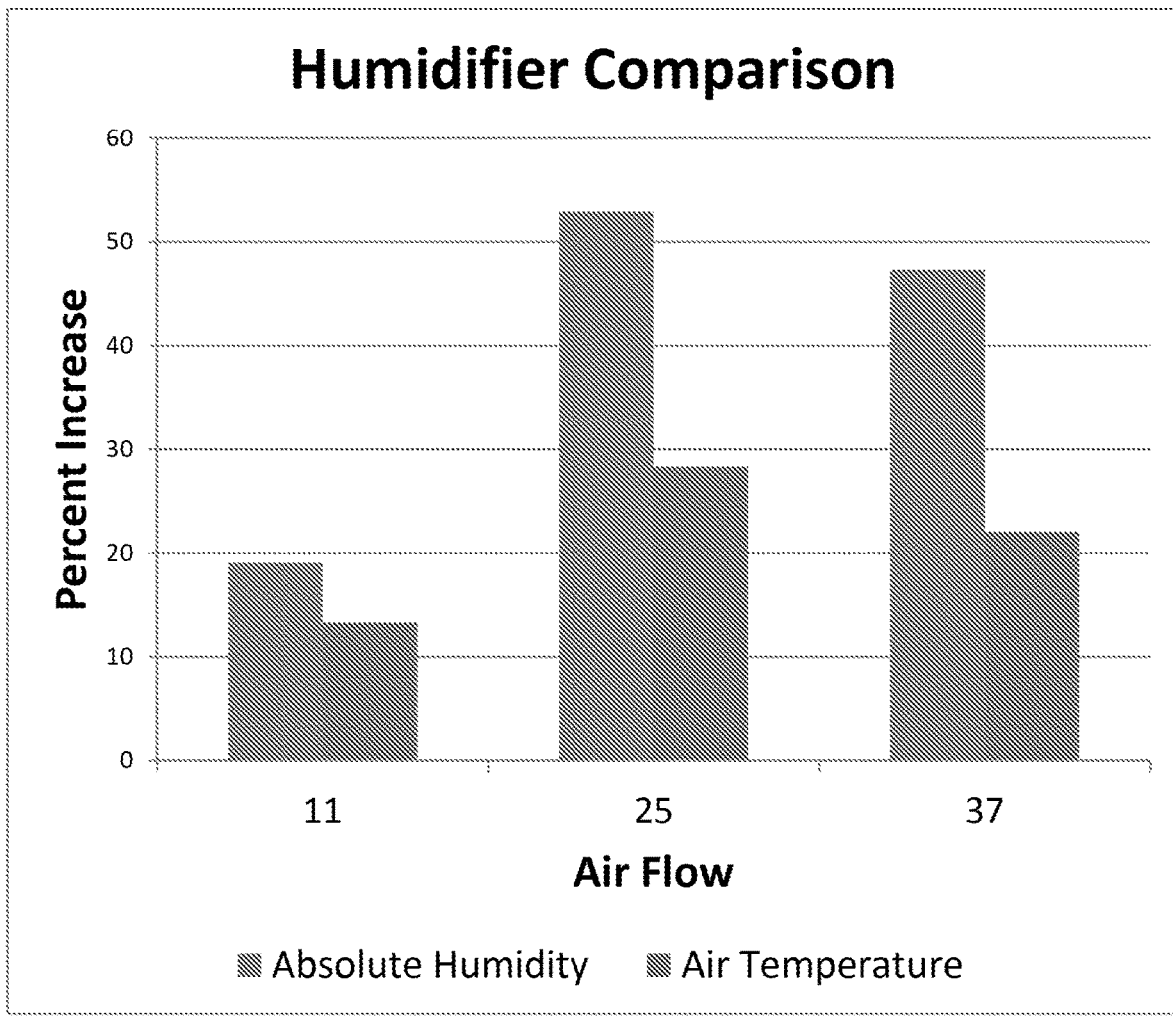
FIG. 5C illustrates quantified percentage increase in both absolute humidity and temperature of humidified air produced by the humidification system according to one embodiment of the invention.

The collected data were presented in Tables 1 and 2, and plotted in FIGS. 5A to 5C. These results show that that the medium flow rate was the optimal among the tested groups. The new humidifier increased the absolute humidity of humidified air by about 50% and increased the temperature of humidified air by about 30%, as compared to the old humidifier.

TABLE 2

Comparison of new and old humidifiers

|  | New Humidifier | Old Humidifier |
|---|---|---|
| Low Flow Rate, Hot Plate: 45 C. | | |
| Average Air Temp | 29.04285714 | 25.62857143 |
| Average Water Vapor Concentration (g/m3) | 25.90714286 | 21.76 |
| % Increase in Water Concentration | 19.05856092 | |
| % Increase in Air Temperature | 13.32218506 | |
| Water Concentration Standard Deviation | 2.229803536 | 0.614731842 |
| Air Temperature Standard Deviation | 1.625686668 | 0.381725406 |
| Medium Flow Rate, Hot Plate: 45 C. | | |
| Average Air Temp | 31.32857143 | 24.41428571 |
| Average Water Vapor Concentration (g/m3) | 28.96 | 18.93857143 |
| % Increase in Water Concentration | 52.90789771 | |
| % Increase in Air Temperature | 28.32065535 | |
| Water Concentration Standard Deviation | 2.231303271 | 2.499262748 |
| Air Temperature Standard Deviation | 1.517359863 | 1.306941176 |

TABLE 1

Humidity and temperature tests at high, medium and low air flow rates

| Time (min) | New Humidifier Air Temperature (Celsius) | New Humidifier Relative Humidity (%) | New Humidifier Water Vapor Concentration | Old Humidifier Air Temperature (Celsius) | Old Humidifier Relative Humidity (%) | Old Humidifier Water Vapor Concentration |
|---|---|---|---|---|---|---|
| Low Flow Rate, Hot Plate: 45 C. | | | | | | |
| 0 | 25.4 | 89 | 20.95 | 25.4 | 92 | 21.66 |
| 10 | 29.3 | 89 | 25.98 | 25.9 | 92 | 22.27 |
| 20 | 30 | 90 | 27.29 | 26.2 | 92 | 22.65 |
| 30 | 29.9 | 90 | 27.15 | 25.7 | 92 | 22.02 |
| 40 | 29.7 | 90 | 26.85 | 25.7 | 91 | 21.78 |
| 50 | 29.6 | 90 | 26.71 | 25.5 | 91 | 21.54 |
| 60 | 29.4 | 90 | 26.42 | 25 | 90 | 20.71 |
| Medium Flow Rate, Hot Plate: 45 C. | | | | | | |
| 0 | 33.3 | 88 | 31.83 | 27.3 | 91 | 23.81 |
| 10 | 33.4 | 88 | 32 | 24.3 | 91 | 20.13 |
| 20 | 31.7 | 89 | 29.57 | 23.6 | 90 | 19.14 |
| 30 | 30.8 | 89 | 28.18 | 23.5 | 87 | 18.39 |
| 40 | 30.3 | 89 | 27.43 | 23.9 | 84 | 17.76 |
| 50 | 30.1 | 89 | 27.14 | 24.1 | 78 | 17.06 |
| 60 | 29.7 | 89 | 26.56 | 24.2 | 74 | 16.28 |
| High Flow Rate, Hot Plate: 45 C. | | | | | | |
| 0 | 27.5 | 85 | 22.49 | 30.5 | 89 | 27.73 |
| 10 | 31.5 | 88 | 28.93 | 24.6 | 90 | 20.25 |
| 20 | 30.1 | 88 | 26.83 | 24.3 | 89 | 19.69 |
| 30 | 29.4 | 88 | 25.83 | 23.9 | 89 | 19.25 |
| 40 | 30.3 | 89 | 27.43 | 23.7 | 87 | 18.60 |
| 50 | 32.4 | 89 | 30.7 | 23.6 | 58 | 12.33 |
| 60 | 32.5 | 89 | 30.86 | 24.5 | 59 | 13.20 |

TABLE 2-continued

Comparison of new and old humidifiers

| | New Humidifier | Old Humidifier |
|---|---|---|
| High Flow Rate, Hot Plate: 45 C. | | |
| Average Air Temp | 30.52857143 | 25.01428571 |
| Average Water Vapor Concentration (g/m3) | 27.58142857 | 18.72 |
| % Increase in Water Concentration | 47.3254483 | |
| % Increase in Air Temperature | 22.04454597 | |
| Water Concentration Standard Deviation | 2.940263189 | 5.099994865 |
| Air Temperature Standard Deviation | 1.780181906 | 2.449781331 |

Example 2

Bacteria Tests

Metal Coating

Antibacterial effect of metal coatings for resisting bacterial growth in the water chamber of the humidification system was examined Particularly, beakers were coated with either copper or silver for two different thicknesses. A Denton DV-502 vacuum evaporator was used for the coating. The diameter for both wires, copper and silver, was 2.032 mm. For a thinner coating, the tungsten basket of the vacuum evaporator was loaded with 75 mm of copper or silver wire. For a thicker coating, 150 mm copper or silver wire was used. The roughing pump was to bring the pressure down for the oil diffusion pump to work. The roughing pump was let run for 10 minutes, and the oil diffusion pump was let run for 5 minutes. Once the vacuum pressure was low enough, the current passed through the tungsten filament was increased to 30 amps for 30 seconds. The beaker was allowed to cool before being removed from the vacuum evaporator.

Bacterial Culture

An antibiotics-resistant E. coli strains was used. 25 µL of bacteria was added to 600 mL of the LB media. The culture was allowed to incubate for 12 hours in a shaking incubator. At the 12 hour mark the bacteria was removed from the incubator and the optical density was measured using a Genysis 20 spectrometer. If the optical density did not reach 0.4, then the culture was allowed to incubate longer, until the optical density was reached. Once the optical density was reached, 110 mL of the culture media was added to each of a thin-copper coated beaker (Cu Thin), a thick-copper coated beaker (Cu Thick), a thin-silver coated beaker (Ag Thin), a thick-silver coated beaker (Ag-thick), and a non-coated beaker (control). The beakers were put on a shaking incubator.

E. coli Cell Density Measurement 1 mL of media was taken from each beaker and put into separate cuvettes at one hour intervals. Each cuvette was put into a spectrometer to examine cell density of the culture. The cell density is measured by turbidity, as turbidity is affect by amount cellular material in the cuvette, which is a product of cell division. The measurement was summarized in Table 3, and plotted in FIG. 6A.

TABLE 3

E. coli Cell Density Measurement

| Hour | Control | Silver-Thin | Silver-Thick | Copper-Thin | Copper-Thick |
|---|---|---|---|---|---|
| 0 | 0.471 | 0.479 | 0.477 | 0.475 | 0.477 |
| 1 | 0.555 | 0.558 | 0.528 | 0.55 | 0.543 |
| 2 | 0.642 | 0.638 | 0.627 | 0.637 | 0.627 |
| 3 | 0.727 | 0.695 | 0.709 | 0.705 | 0.706 |
| 4 | 0.825 | 0.803 | 0.802 | 0.78 | 0.787 |
| 5 | 0.914 | 0.813 | 0.876 | 0.849 | 0.869 |
| 6 | 0.996 | 0.874 | 0.945 | 0.919 | 0.938 |
| 7 | 1.078 | 0.914 | 1.012 | 0.972 | 1.002 |

Figure 6A:
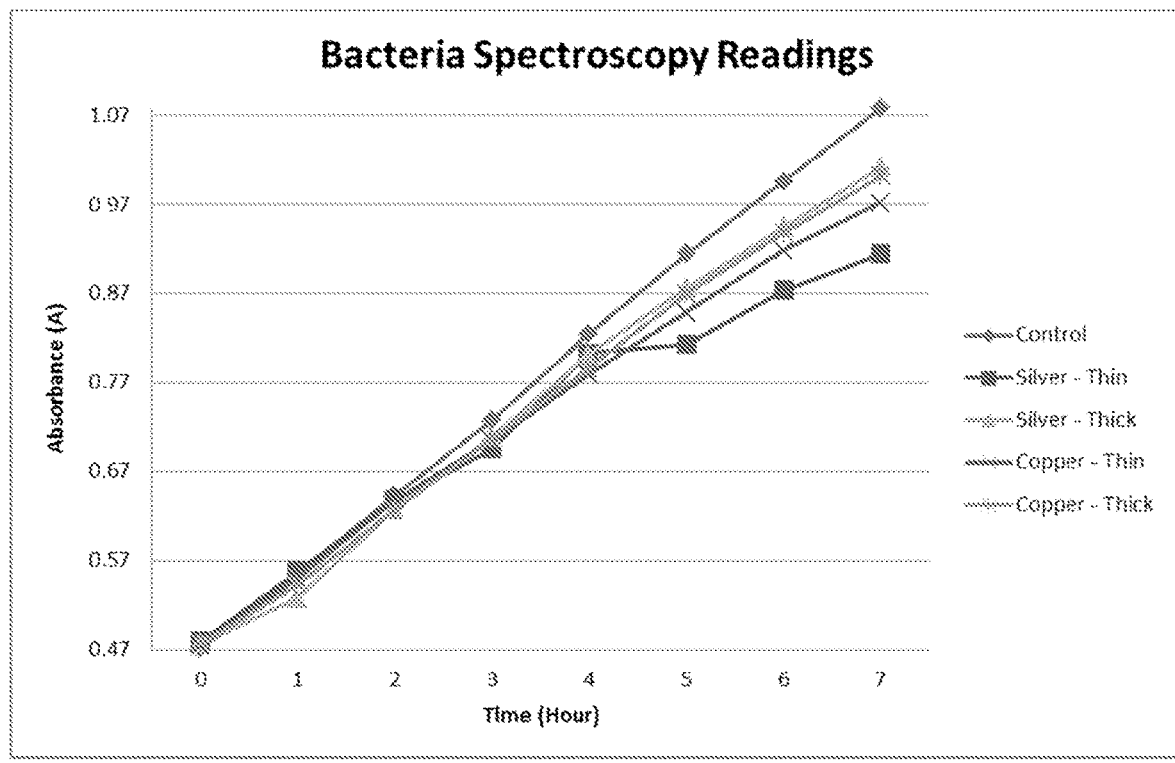
FIG. 6A illustrates bacterial spectroscopy readings of absorbance of bacterial cultures grown in non-coated, silver-coated and copper-coated containers.

As shown in FIG. 6A, thin silver produced the least absorbance; therefore the cells divided the least in silver. Also, the Control group had almost linear growth.

E. coli Cell Death Measurement

Turbidity of the culture media does not directly reflect cell death induced by the metal exposure. Hence, to measure cell death in the culture media taken at each hour, the cells are stain with trypan Blue, which specifically dyes dead bacterial cells. The concentration of trypan blue is 0.4% suspended in a 1.times.PBS solution.

Particularly, media aliquots from each cuvette were taken, and 10 µL of trypan blue solution was added to 10 µL aliquot of cell suspension in a 1.5 mL micro-centrifuge tube. The mixture was aspirated 4 times to ensure a homogeneous mixture. 10 µL of the mixture was loaded into the hemacytometer, and the cell numbers were counted.

A second aliquot of the culture media was used for florescent analysis. Particularly, 30 µL of the cell suspension was added to a petri dish. The cells were allowed to adhere to the surface of the dish for 10 minutes. Once the cells adhered, 1.times.PBS was used to wash out the LB culture media. A pipette tip was aimed slightly above the center of the cell suspension so that the PBS gently washed the LB broth away from the cells. 2 washes of 0.5 mL PBS were sufficient. Next, clean pipette tip was used to suck up the PBS and LB mixture. The pipette tip was disposed in a 10% bleach solution. 40 µL of a prodium iodide solution was added to the cells and mixture was covered with a cover slip. The cells were stained in propidium iodide for 10 minutes in dark. An Olympus BX-51 microscope was used to take images of stained cells. Images were taken at 10× magnification. The first image was taken in bright field (BF) and the second was taken using green laser excitation, the WGS filter. The reason for using BF in addition to the WGS was to make sure there were cells present in the sample, i.e. to check the quality of the staining. The results are shown in FIG. 6B to 6E. All WGS images have been gray scaled.

Figure 6B:
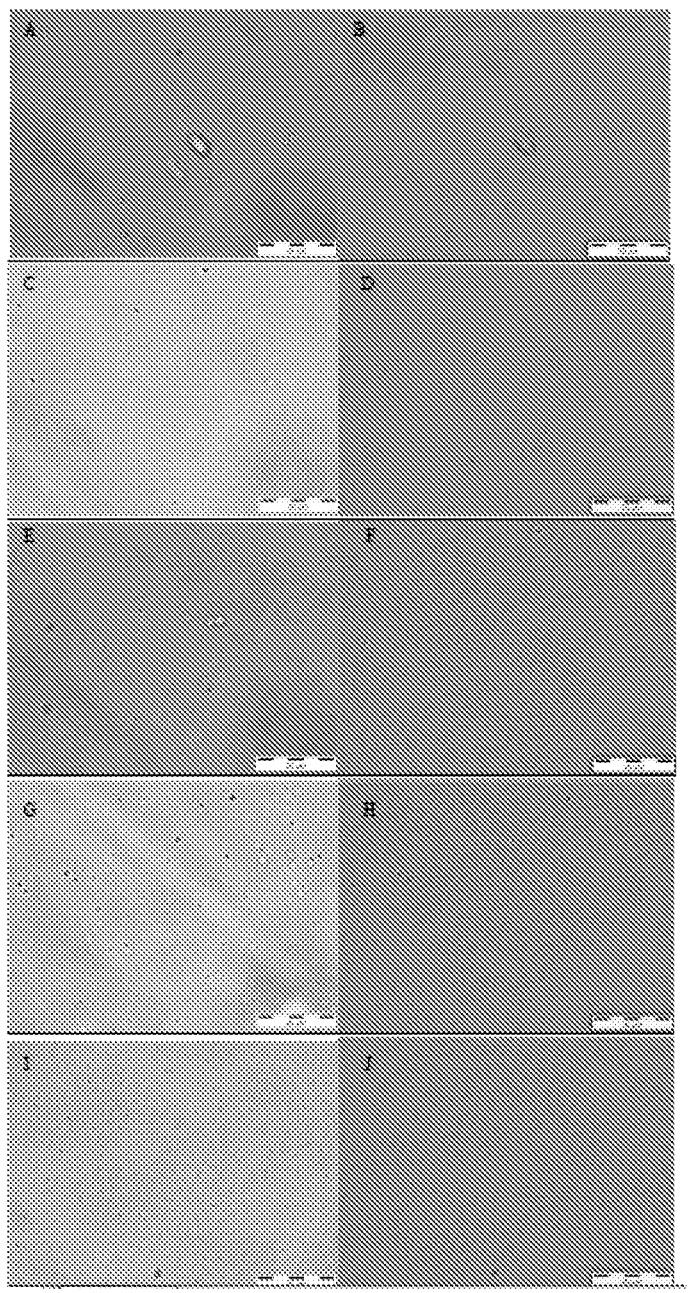
FIG. 6B illustrates stains of dead bacterial in cultures grown in non-coated, silver-coated and copper-coated containers. This figure shows dead bacterial after 1 hour of incubation. From A to J: Control BF, Control WGS, Thin Silver BF, Thin Silver WGS, Thick Silver, BF, Thick Silver WGS, Thin Copper BF, Thin Copper WGS, Thick Copper BF, Thick Copper WGS.

FIG. 6B shows the first hour of incubation on the metal substrates and the control. Bright fringes in the Control are air bubbles due to incorrect loading of the sample. The thin coatings of both metals were killing bacteria faster than the thick coatings, shown by more black cells in the WGS. Also, at this time the thin copper had completely sheared off the beaker. The thin silver has missing pieces.

Figure 6C:
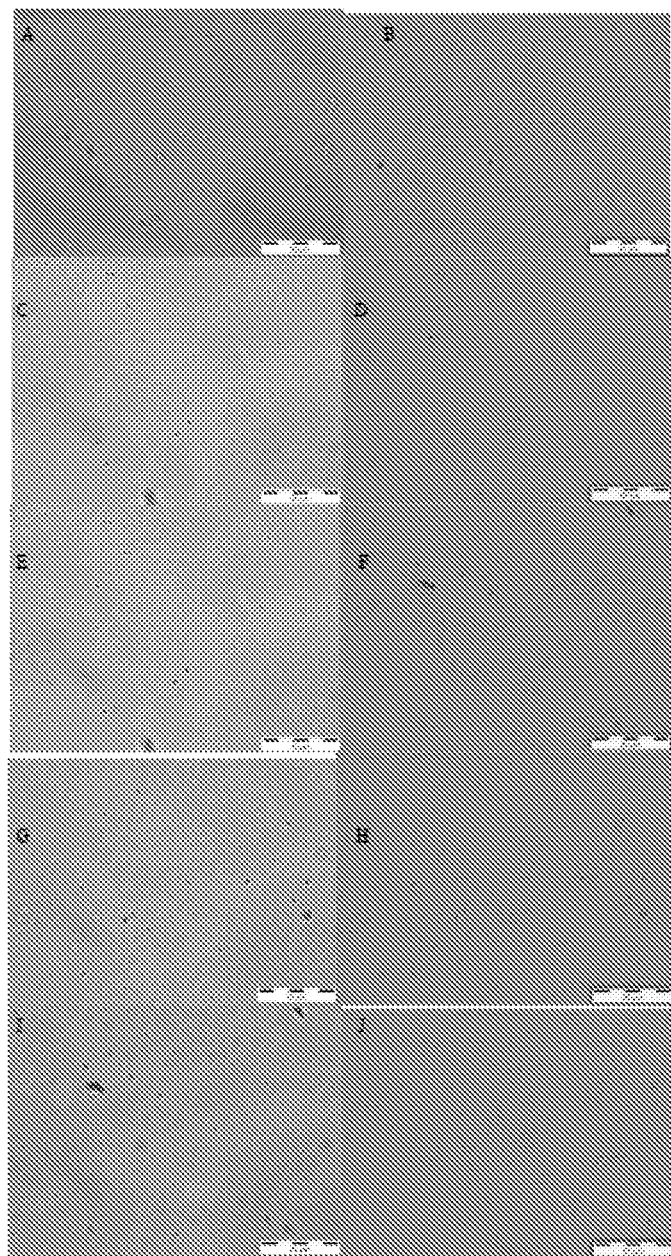
FIG. 6C illustrates stains of dead bacterial in cultures grown in non-coated, silver-coated and copper-coated containers. This figure shows dead bacterial after 3 hours of incubation. From A to J: Control BF, Control WGS, Thin Silver BF, Thin Silver WGS, Thick Silver, BF, Thick Silver WGS, Thin Copper BF, Thin Copper WGS, Thick Copper BF, Thick Copper WGS.

FIG. 6C shows the third hour of incubation. Some of the cells were killed mid-divide in the thick-Ag coated beaker, while some were living mid-divide. In the Bright Field image of the Cu thick samples, there are concentrated DNA due to cells preparing for division. This shows they were killed mid-division.

Figure 6D:
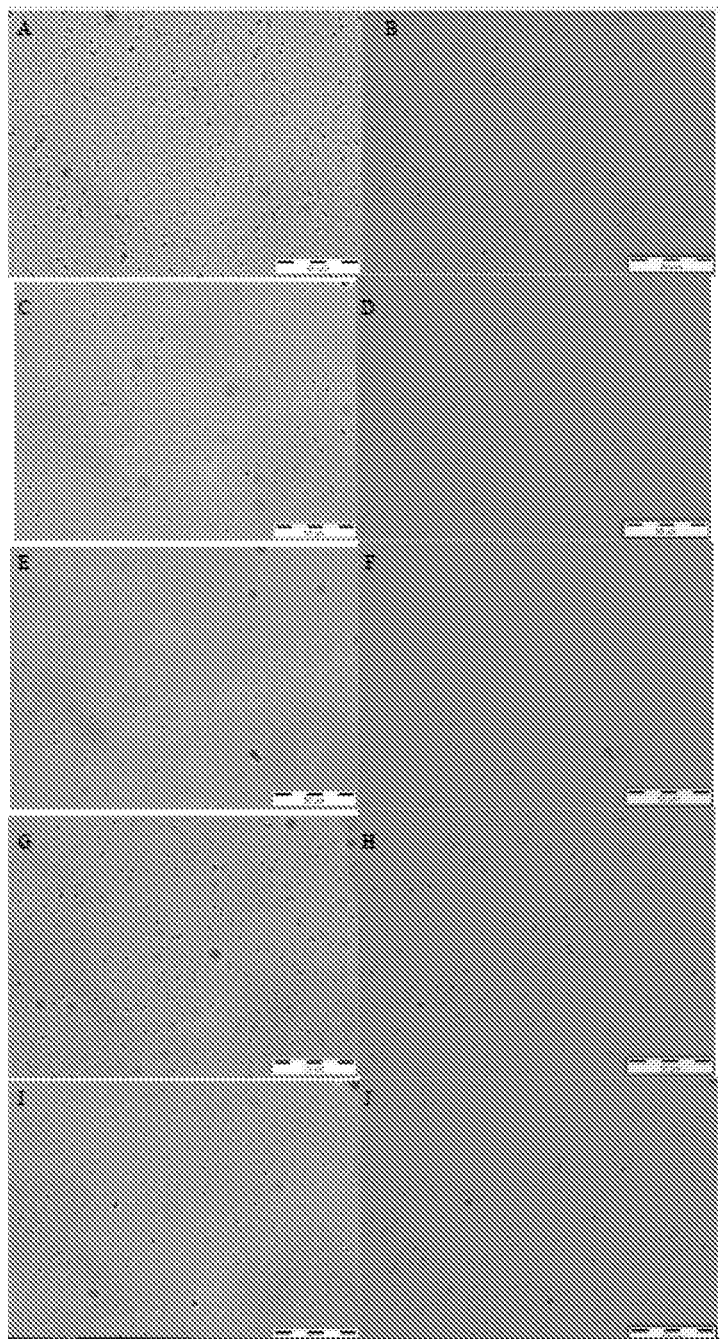
FIG. 6D illustrates stains of dead bacterial in cultures grown in non-coated, silver-coated and copper-coated containers. This figure shows dead bacterial after 5 hours of incubation. From A to J: Control BF, Control WGS, Thin Silver BF, Thin Silver WGS, Thick Silver, BF, Thick Silver WGS, Thin Copper BF, Thin Copper WGS, Thick Copper BF, Thick Copper WGS.

FIG. 6D shows the fifth hour of incubation. There was a significant amount of cell death in the control. The amount of cell staining in the silver substrates decreased while the cell staining in both copper substrates increased. There were fewer cells present in the BF images of the silver substrates. Fewer cells present means less chances for staining.

Figure 6E:
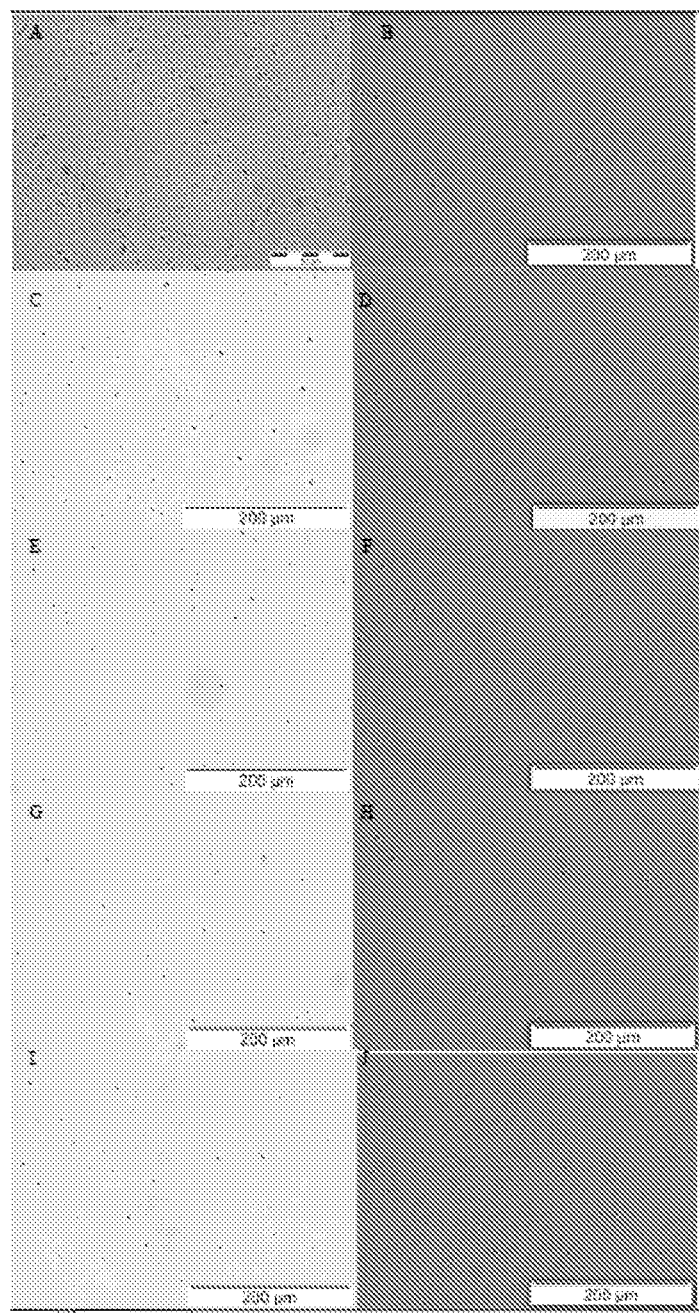
FIG. 6E illustrates stains of dead bacterial in cultures grown in non-coated, silver-coated and copper-coated containers. This figure shows dead bacterial after 7 hour of incubation. From A to J: Control BF, Control WGS, Thin Silver BF, Thin Silver WGS, Thick Silver, BF, Thick Silver WGS, Thin Copper BF, Thin Copper WGS, Thick Copper BF, Thick Copper WGS.

FIG. 6E shows the seventh hour of incubation. At the final hour all the cells were dead and it cannot be determined if they died due to starvation or oxidation.

Example 3. Heat Blanket Tests

To test the efficiency in reducing condensation by the heat blanket tubing. Applicant tested and compared the tubes equipped with heating wires (conventional), tubes equipped with both heating wires and heating blanket, bare tubes and tubes equipped with only heating blanket. These tests were completed for one and a half hour interval and were repeated three times each. The average was then calculated to measure for condensation and water build up. To do so, the initial weight of the tube was documented and the final weight as well, after the one hour and a half of running the system was complete. To portray the effects of room temperature change due to room ventilation, the addition of a fan, blowing with a constant cold air flow, was directed towards the lowest point of the tube. This simulates the scenarios which can occur in a hospital.

As shown in FIGS. 8A, 8B, 9A and 9B, among all tested conditions, the bare tubes yielded the largest amount of condensed water, which was an average of 27.5 g water. The water in this test formed major water pockets that completely blocked the passage of the humidified air. The conventional heat-wire tube produced an average of 3 g water, and the tubes equipped with both a heat wire and a heat blanket yielded an average of 0.7 g of condensed water. The tube equipped with only the heat blanket produced an average of 4 g water.

Figure 9A:
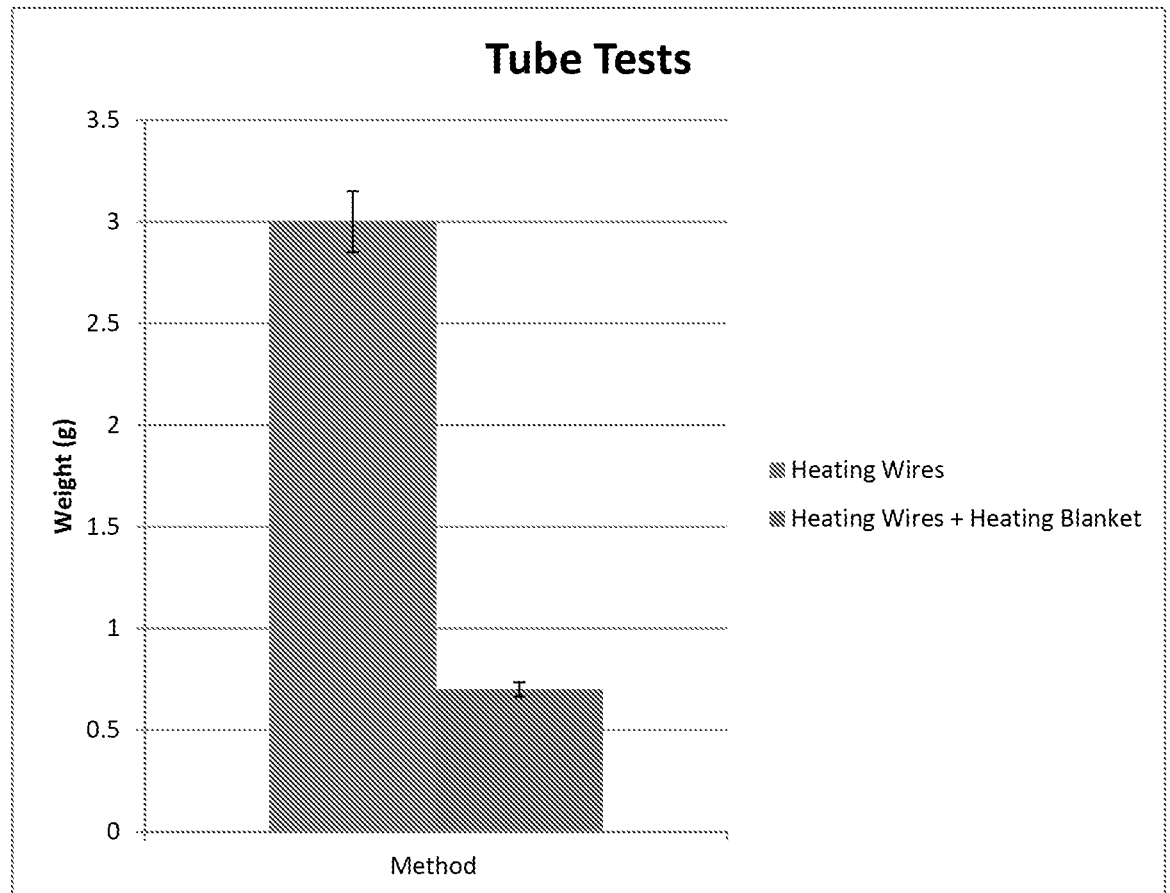
FIG. 9A shows the weights of condensed water collected from the conventional heat wire tube and a tube equipped with both a heat wire and a heat blanket.
Figure 9B:
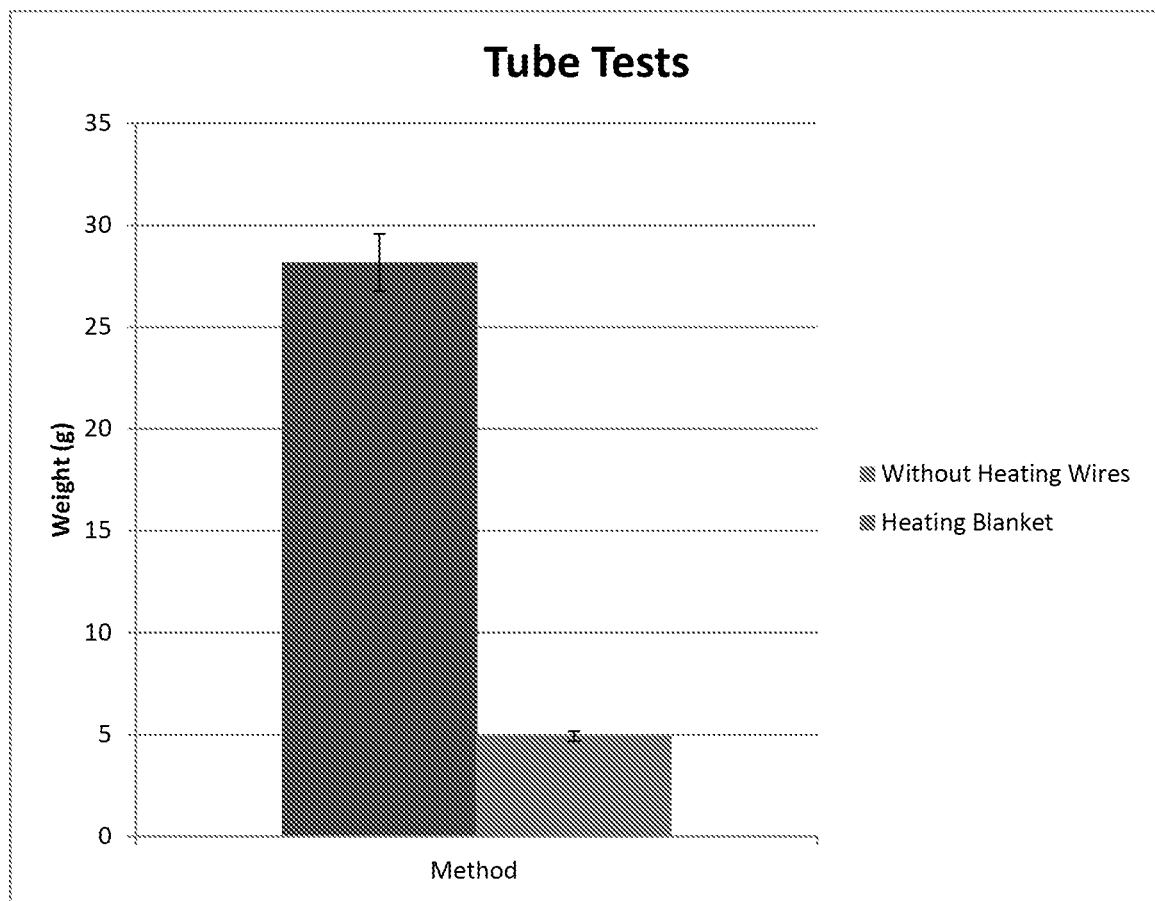
FIG. 9B shows the weights of condensed water collected from a bare tube and a tube equipped with a heat blanket.
Figure 9C:
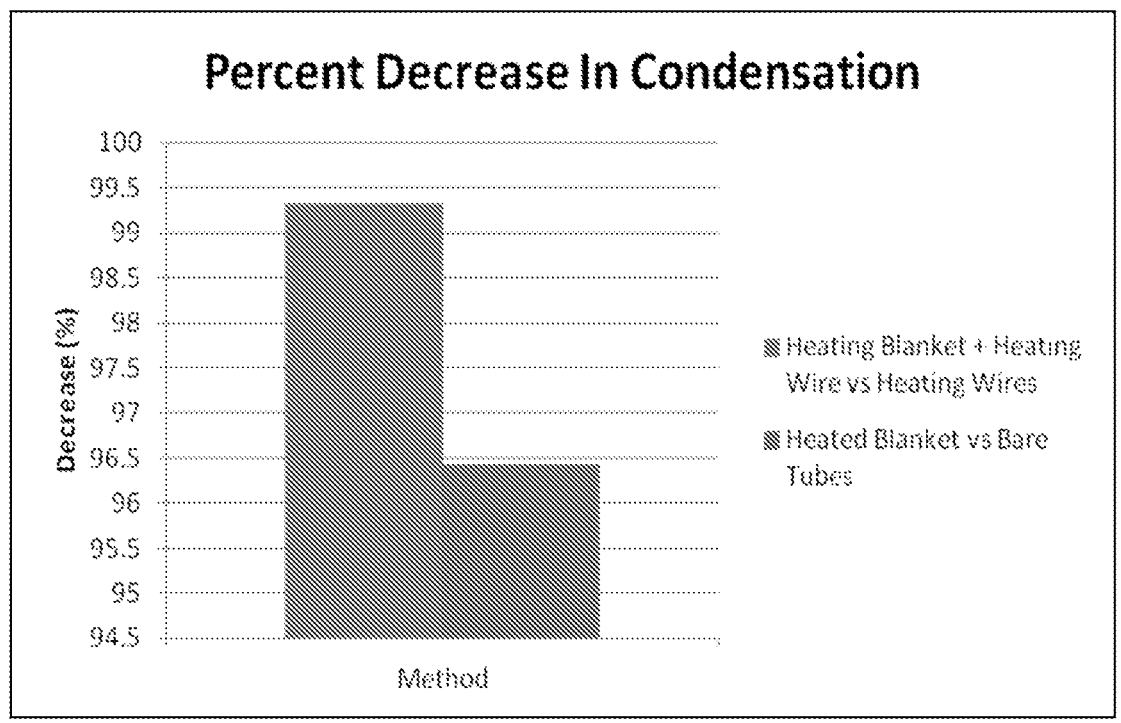
FIG. 9C shows the percentage changes (decrease) in condensation for tubes equipped with a heat blanket.

As shown in FIG. 9C, in the tests that compared the conventional tube equipped with only the heat wire and the tube equipped with both the heat wire and the heat blanket, the data yielded a 2.3 g or 99.4% decrease in the amount of condensed water with the use of the heat blanket. In the tests that compared the bare tube and tube equipped with only heat blanket, the data yielded a 23.5 g or 96.4% decrease in the amount of condensed water. The tube equipped with both the heat wire and heat blanket produced the optimal decrease in condensation.

Figure 10A:
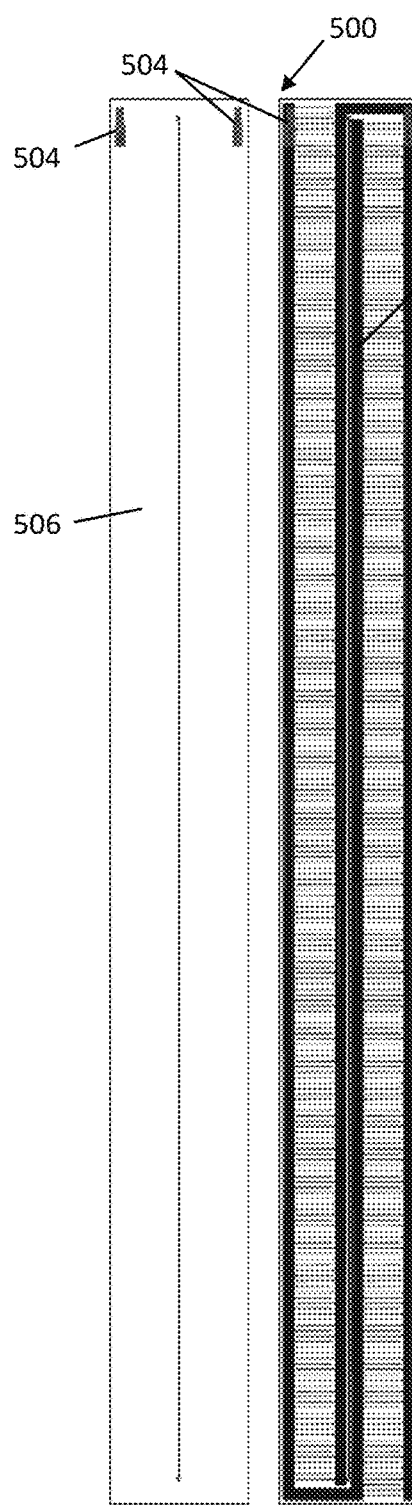
FIGS. 10A and 10B show a transparent polymer-based heating element sleeve for the insolation of a tube delivering heated and humidified gas.
Figure 10B:
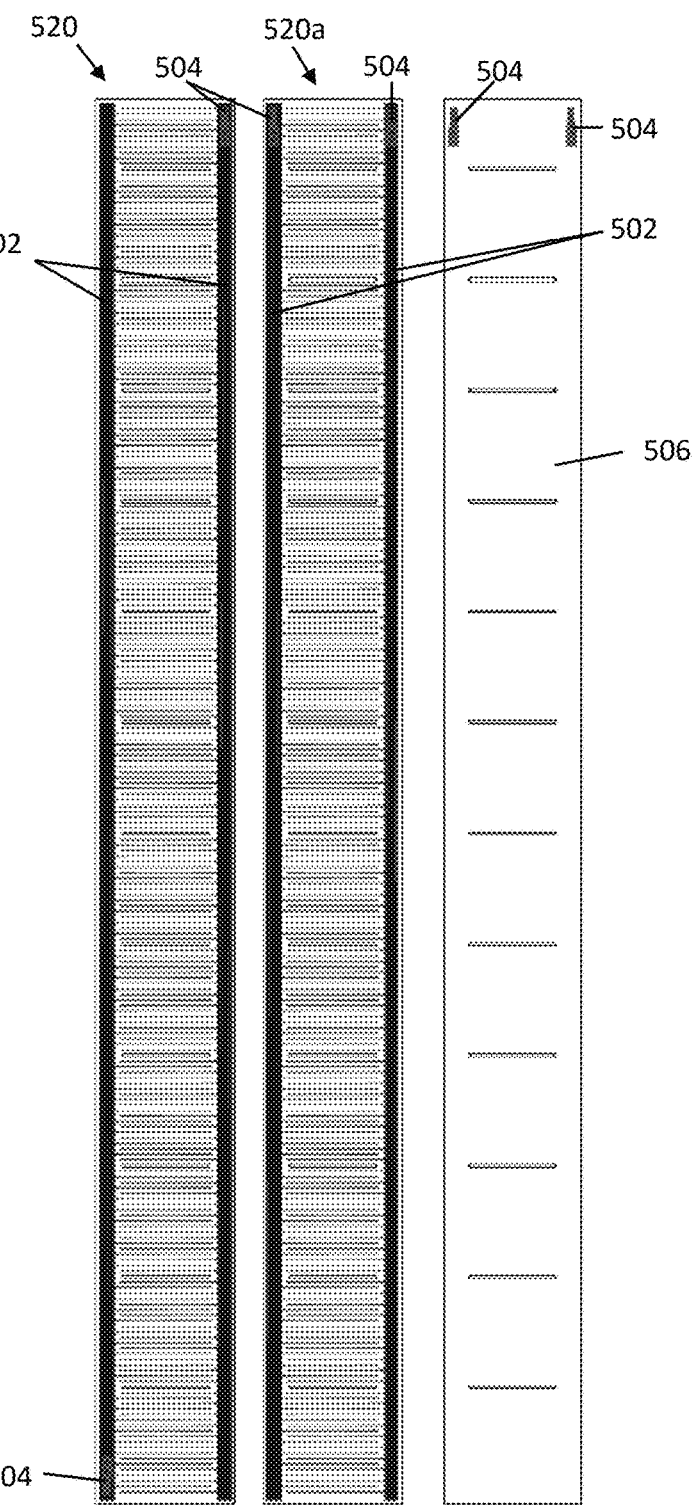

FIGS. 10A and 10B show a transparent polymer-based heating element sheet or sleeve 500, 520, respectively, for the insulation and heating of a tube delivering heated and humidified gas. FIG. 10A the transparent polymer-based heating element sheet or sleeve 500 has a positive-temperature coefficient (PTC) heating element(s) 502 in which the pads 504 for connecting to a source of electricity are on the same end of the transparent polymer-based heating element sheet or sleeve 500, with a top view (left) and a bottom view (right). In this embodiment, the heating element(s) 502 follows a serpentine path as shown, with the conductive paths create two heating elements, side by side, along of the flexible substrate 506. FIG. 10B shows a transparent polymer-based heating element sheet or sleeve 520 with the positive-temperature coefficient (PTC) heating element(s) 502 of the present invention in which the pads 504 are on an opposite end of the transparent polymer-based heating element sheet or sleeve 520, in which with the pads 504 on opposite ends of the transparent polymer-based heating element sheet or sleeve 520 (left). The middle view shows another alternative in which the pads 504 on the same end of the transparent polymer-based heating element sheet or sleeve 520a (middle). The heating element(s) 502 in either of these embodiments traverse from one side of the flexible substrate 506. The opposite side of either embodiment is shown (right), in this case having the connecting pads on the same side. The device is manufactured and distributed as a sheet or sleeve, but the nurses/users will be enveloping the ventilator tube with the sheet or sleeve. The heating and length parameters include, e.g., at least partially surrounding a tube with the transparent polymer-based heating element sheet or sleeve to maintain a heat slightly above body temperature, 98.6° F./37° C. In certain embodiments, the transparent polymer-based heating element sleeve can even maintain a temperature between 20° C. to 60° C. That temperature range is outside of the useful medical range, provides protection for medical use. While the dimensions will depend on tube or use, in certain non-limiting examples can be, e.g., longer than 10 centimeters and shorter than 3 meters. The heating element(s) 502 can be printed on the flexible substrate 506 as shown in FIGS. 10A and 10B but can also be printed along a longitudinal axis of the transparent polymer-based heating element sheet or sleeve 500, 520.

Based on FIGS. 10 and 10B, the present invention includes a transparent or semi-transparent polymer-based heating element sleeve or sheet for the insulation of a tube delivering heated and humidified gas to a subject, comprising: a self-regulated heater and self-limiting heater, wherein the tubing is enveloped by the transparent heating sleeve, wherein the heating sleeve maintains at least one of: rates of relative humidity, absolute humidity and gas temperature, and wherein the heating sleeve envelops the tubing of inspiratory or expiratory limbs or ports connected to a mechanical ventilator providing gas to a subject. The heating sleeve or sheet can further comprise a protective or connecting tube fitting over or enclosing the inspiratory or expiratory limbs or ports breathing tubes. Also, the heating sleeve or sheet further comprises externally or internally insulating the tube which delivers heated and humidified gas to a subject. Moreover, the heating sleeve or sheet is a transparent polymer-based heating element. In one aspect, the heating sleeve or sheet generates heat through a positive-temperature coefficient (PTC) heating element. In another aspect, a material within the heating sleeve or sheet consists of the PTC heating elements that are embedded in the transparent polymer. In another aspect, the heating sleeve or sheet is self-regulating, wherein each of one or more independent heating elements maintain a constant temperature without a need of electronic regulation. In another aspect, the heating sleeve or sheet is self-limiting, wherein the heating sleeve or sheet cannot exceed a certain temperature in any point, wherein the heating sleeve or sheet does not require overheating protection. In another aspect, the heating sleeve or sheet maintains a temperature between 20° C. to 60° C. in the tube. In another aspect, the heating sleeve or sheet maintains a temperature between 36° to 39° C. in the tube.

The present invention also includes a kit for retrofitting a tube for delivering heated and humidified gas to a subject, the kit comprising: a transparent polymer-based heating element sleeve or sheet for the insulation of a tube delivering heated and humidified gas to a subject, comprising: a self-regulated heater and self-limiting heater, wherein the tubing is enveloped by the transparent heating sleeve, wherein the heating sleeve maintains at least one of: rates of relative humidity, absolute humidity and gas temperature, and wherein the heating sleeve envelops the tubing of inspiratory or expiratory limbs or ports connected to a mechanical ventilator providing gas to a subject. The kit further comprises a protective or connecting tube fitting over or enclosing the inspiratory or expiratory limbs or ports breathing tubes. The tube which delivers heated and humidified gas to a subject can also be insulated externally or internally, or both. In one aspect, the heating sleeve or sheet generates heat through a positive-temperature coefficient (PTC) heating element. In another aspect, a material within the heating sleeve or sheet consists of the PTC heating elements that are embedded in the transparent polymer. The heating sleeve or sheet can be self-regulating, wherein each of one or more independent heating elements maintain a constant temperature without a need of electronic regulation. If the heating sleeve or sheet is self-limiting, the heating sleeve or sheet cannot exceed a certain temperature in any point, wherein the heating sleeve or sheet does not require overheating protection. In a further aspect, the heating sleeve or sheet maintains a temperature between 20° C. to 60° C. in the tube. In one aspect, the heating sleeve or sheet maintains a temperature between 36° to 39° C. in the tube.

The present invention also includes a system for humidifying ventilator air, comprising a chamber, a base, a central cylinder and a helical inclining plane, wherein the chamber comprises an air inlet for receiving air from an air source, an air outlet for releasing humidified air, and an inner wall; wherein the base comprises an inner surface, the inner surface and the inner wall forming a sealed space capable of holding water and air; wherein the central cylinder comprises a bottom and a side, the bottom attaching to the inner surface of the base; wherein the helical inclining plane comprises a helical center, an inner edge and an outer edge, the central cylinder passing through the helical inclining plane at the helical center; the inner edge attaching to the side of the central cylinder; wherein the outer edge of the helical inclining plane engages with the inner wall of the chamber to form a helical inclining tunnel, a lower end of the tunnel opening towards the air inlet and a upper end of the tunnel opening towards the air outlet; and transparent or semi-transparent polymer-based heating element sleeve or sheet for the insulation of a tube delivering heated and humidified gas to a subject, comprising: a self-regulated heater and self-limiting heater, wherein the tubing is enveloped by the transparent heating sleeve, wherein the heating sleeve maintains at least one of: rates of relative humidity, absolute humidity and gas temperature, and wherein the heating sleeve envelops the tubing of inspiratory or expiratory limbs or ports connected to a mechanical ventilator providing gas to a subject.

Finally, the present invention also includes a method for heating and humidifying ventilator air, comprising a chamber, a base, a central cylinder, a helical inclining plane, and a tube comprising: providing the chamber comprises an air inlet for receiving air from an air source, an air outlet for releasing humidified air, and an inner wall; wherein the base comprises an inner surface, the inner surface and the inner wall forming a sealed space capable of holding water and air; wherein the central cylinder comprises a bottom and a side, the bottom attaching to the inner surface of the base; wherein the helical inclining plane comprises a helical center, an inner edge and an outer edge, the central cylinder passing through the helical inclining plane at the helical center; the inner edge attaching to the side of the central cylinder; wherein the outer edge of the helical inclining plane engages with the inner wall of the chamber to form a helical inclining tunnel, a lower end of the tunnel opening towards the air inlet and a upper end of the tunnel opening towards the air outlet; and surrounding at least partially the tube with a transparent or semi-transparent polymer-based heating element sleeve or sheet for the insulation of a tube delivering heated and humidified gas to a subject, comprising: a self-regulated heater and self-limiting heater; wherein the tubing is enveloped by the transparent heating sleeve; wherein the heating sleeve maintains at least one of: rates of relative humidity, absolute humidity and gas temperature; and wherein the heating sleeve envelops the tubing of inspiratory or expiratory limbs or ports connected to a mechanical ventilator providing gas to a subject.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Various embodiments of the invention can specifically include or exclude any of these variations or elements.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Certain embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least±1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention (s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

What is claimed is:

1. A transparent or semi-transparent polymer-based heating sleeve or sheet for the insulation of a tube for delivering heated and humidified gas to a subject, comprising:
   a self-regulated and self-limiting heater;
   wherein the heating sleeve or sheet is configured to maintain relative humidity, absolute humidity, and gas temperature within the tube;
   wherein the heating sleeve or sheet is further configured to envelop the tube; and
   wherein the heating sleeve or sheet comprises two opposing, generally U-shaped and interlocked heating elements with electrical contacts on a same end of the heating sleeve or sheet.

2. The heating sleeve or sheet of claim 1, further comprising external or internal insulation for the tube which delivers heated and humidified gas to the subject.

3. The heating sleeve or sheet of claim 1, wherein the heating sleeve or sheet is a transparent polymer-based heating sleeve or sheet.

4. The heating sleeve or sheet of claim 1, wherein the heating elements are positive-temperature coefficient (PTC) heating elements.

5. The heating sleeve or sheet of claim 4, wherein a material of the heating sleeve or sheet consists of the PTC heating elements embedded in a transparent polymer.

6. The heating sleeve or sheet of claim 1, wherein the heating sleeve or sheet is self-regulating, wherein each the heating elements is configured to maintain a constant temperature without a need of electronic regulation.

7. The heating sleeve or sheet of claim 1, wherein the heating sleeve or sheet is self-limiting, wherein the heating sleeve or sheet cannot exceed a certain temperature in any point, wherein the heating sleeve or sheet does not require overheating protection.

8. The heating sleeve or sheet of claim 1, wherein the heating sleeve or sheet is configured to maintain a temperature between 20° C. to 60° C. in the tube, or wherein the heating sleeve or sheet is configured to maintain a temperature between 36° C. to 39° C. in the tube.

9. A system for humidifying ventilator air, comprising:
   a chamber, a base, a central cylinder and a helical inclining plane, comprising:
   wherein the chamber comprises an air inlet for receiving air from an air source, an air outlet for releasing humidified air, and an inner wall;
   wherein the base comprises an inner surface, the inner surface and the inner wall forming a sealed space capable of holding water and air;
   wherein the central cylinder comprises a bottom and a side, the bottom attaching to the inner surface of the base;
   wherein the helical inclining plane comprises a helical center, an inner edge and an outer edge, the central cylinder passing through the helical inclining plane at the helical center; the inner edge attaching to the side of the central cylinder;
   wherein the outer edge of the helical inclining plane engages with the inner wall of the chamber to form a helical inclining tunnel, a lower end of the tunnel opening towards the air inlet and a upper end of the tunnel opening towards the air outlet; and
   a transparent or semi-transparent polymer-based heating sleeve or sheet for the insulation of a tube for delivering heated and humidified gas to a subject, comprising:
   a self-regulated and self-limiting heater,
   wherein the tube is enveloped by the transparent heating sleeve,
   wherein the heating sleeve or sheet is configured to maintain relative humidity, absolute humidity, and gas temperature within the tube,
   wherein the tube comprises inspiratory or expiratory limbs or ports connected to a mechanical ventilator providing gas to the subject, and
   wherein the heating sleeve or sheet comprises two opposing, generally U-shaped and interlocked heating elements with electrical contacts on a same end of the heating sleeve or sheet.

10. A method for heating and humidifying ventilator air, comprising providing a chamber, a base, a central cylinder, a helical inclining plane, and a tube comprising:

providing the chamber which comprises an air inlet for receiving air from an air source, an air outlet for releasing humidified air, and an inner wall;

wherein the base comprises an inner surface, the inner surface and the inner wall forming a sealed space capable of holding water and air, wherein the base is a metal heat plate;

wherein the central cylinder comprises a bottom and a side, the bottom attaching to the inner surface of the base;

wherein the helical inclining plane comprises a helical center, an inner edge and an outer edge, the central cylinder passing through the helical inclining plane at the helical center; the inner edge attaching to the side of the central cylinder;

wherein the outer edge of the helical inclining plane engages with the inner wall of the chamber to form a helical inclining tunnel, a lower end of the tunnel opening towards the air inlet and a upper end of the tunnel opening towards the air outlet; and surrounding at least partially the tube with a transparent or semi-transparent polymer-based heating sleeve or sheet for insulation of the tube for delivering heated and humidified gas to a subject, the heating sleeve or sheet comprising:

a self-regulated and self-limiting heater;

wherein the tube is enveloped by the transparent heating sleeve;

wherein the heating sleeve or sheet is configured to maintain relative humidity, absolute humidity, and gas temperature within the tube;

wherein the tube comprises inspiratory or expiratory limbs or ports connected to a mechanical ventilator providing gas to the subject; and wherein the heating sleeve or sheet comprises two opposing, generally U-shaped and interlocked heating elements with electrical contacts on a same end of the heating sleeve or sheet.

\* \* \* \* \*